US 12,089,941 B2

(12) United States Patent
Bickford et al.

(10) Patent No.: US 12,089,941 B2
(45) Date of Patent: Sep. 17, 2024

(54) MINIATURE ELECTRIC FIELD DETECTOR

(71) Applicant: THE CHARLES STARK DRAPER LABORATORY, INC., Cambridge, MA (US)

(72) Inventors: James A. Bickford, Winchester, MA (US); Jesse J. Wheeler, Revere, MA (US); Stephanie Lynne Golmon, Arlington, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 1221 days.

(21) Appl. No.: 16/819,705

(22) Filed: Mar. 16, 2020

(65) Prior Publication Data

US 2020/0289013 A1 Sep. 17, 2020

Related U.S. Application Data

(60) Provisional application No. 62/819,222, filed on Mar. 15, 2019.

(51) Int. Cl.
*B81B 5/00* (2006.01)
*A61B 5/00* (2006.01)
(Continued)

(52) U.S. Cl.
CPC .............. *A61B 5/296* (2021.01); *A61B 5/282* (2021.01); *A61B 5/341* (2021.01); *A61B 5/6832* (2013.01);
(Continued)

(58) Field of Classification Search
CPC ...... A61B 5/24–297; A61B 2562/0214; G01R 29/12–14; B81B 5/00; B82B 2201/0214
(Continued)

(56) References Cited

U.S. PATENT DOCUMENTS 4,380,735 A  4/1983 Bell
4,439,732 A  3/1984 Hesterman et al.
(Continued)

FOREIGN PATENT DOCUMENTS

CN  102879655 A  1/2013
CN  103390478 A  11/2013
(Continued)

OTHER PUBLICATIONS

International Search Report and Written Opinion in application No. PCT/US2018/025856 dated Jul. 30, 2018.
(Continued)

*Primary Examiner* — Joseph A Stoklosa
*Assistant Examiner* — Brian M Antiskay
(74) *Attorney, Agent, or Firm* — Brooks Kushman P.C.

(57) ABSTRACT

According to various aspects, a sensor system is provided comprising a first substrate configured to be coupled to a user, an electric field detector to detect a user electric field and comprising a second substrate, a proof mass positioned above the second substrate, one or more electrodes coupled to the second substrate, and a control circuit coupled to the one or more electrodes, the control circuit being configured to determine a change in capacitance between the proof mass and each electrode responsive to torsional movement of the proof mass responsive to the electric field, and a controller coupled to the first substrate and being configured to receive, from the detector, information indicative of each change in capacitance between the proof mass and each electrode, and determine, based on the information, characteristics of the electric field in at least two dimensions.

18 Claims, 17 Drawing Sheets

(51) Int. Cl.

| | |
|---|---|
| *A61B 5/282* | (2021.01) |
| *A61B 5/296* | (2021.01) |
| *A61B 5/341* | (2021.01) |
| *G01R 29/12* | (2006.01) |
| *A61B 5/291* | (2021.01) |
| *A61B 5/316* | (2021.01) |
| *G01R 33/028* | (2006.01) |

(52) U.S. Cl.
CPC ............... *A61B 5/291* (2021.01); *A61B 5/316* (2021.01); *A61B 2560/0247* (2013.01); *A61B 2562/0214* (2013.01); *A61B 2562/028* (2013.01); *G01R 33/0286* (2013.01)

(58) Field of Classification Search
USPC ....................................................... 600/382
See application file for complete search history.

(56) References Cited

U.S. PATENT DOCUMENTS

| | | | |
|---|---|---|---|
| 4,600,883 A | | 7/1986 | Egli et al. |
| 4,670,092 A | | 6/1987 | Motamedi |
| 5,224,380 A | | 7/1993 | Paik |
| 5,908,986 A | | 6/1999 | Mitamura |
| 5,945,898 A | | 8/1999 | Judy et al. |
| 5,987,986 A | * | 11/1999 | Wyse ................ G01C 19/5719 |
| | | | 73/504.12 |
| 6,028,773 A | | 2/2000 | Hundt |
| 6,250,156 B1 | | 6/2001 | Seshia et al. |
| 6,429,652 B1 | | 8/2002 | Allen et al. |
| 6,487,864 B1 | | 12/2002 | Platt et al. |
| 6,670,809 B1 | | 12/2003 | Edelstein et al. |
| 6,874,363 B1 | | 4/2005 | Foote et al. |
| 7,185,541 B1 | | 3/2007 | Edelstein |
| 7,231,094 B2 | | 6/2007 | Bickford et al. |
| 7,394,245 B2 | | 7/2008 | Brunson et al. |
| 7,642,692 B1 | | 1/2010 | Pulskamp |
| 7,773,228 B1 | | 8/2010 | Hollingsworth et al. |
| 7,972,888 B1 | | 7/2011 | Li et al. |
| 8,205,497 B1 | | 6/2012 | Okandan et al. |
| 8,674,689 B1 | | 3/2014 | Nielson et al. |
| 8,701,490 B2 | | 4/2014 | Jiang et al. |
| 9,182,454 B1 | | 11/2015 | Williams et al. |
| 10,531,805 B2 | | 1/2020 | Bickford et al. |
| 10,564,200 B2 | | 2/2020 | Bickford et al. |
| 10,585,150 B2 | | 3/2020 | Bickford et al. |
| 2002/0162947 A1 | | 11/2002 | Weitekamp et al. |
| 2003/0140699 A1 | | 7/2003 | Pike et al. |
| 2003/0200807 A1 | | 10/2003 | Hulsing |
| 2004/0187578 A1 | | 9/2004 | Malametz et al. |
| 2005/0234329 A1 | | 10/2005 | Kraus et al. |
| 2006/0032306 A1 | | 2/2006 | Robert |
| 2006/0283246 A1 | | 12/2006 | Weinberg et al. |
| 2007/0029629 A1 | | 2/2007 | Yazdi |
| 2007/0096729 A1 | | 5/2007 | Brunson et al. |
| 2010/0005884 A1 | | 1/2010 | Weinberg et al. |
| 2010/0099942 A1 | | 4/2010 | Portelli |
| 2010/0108478 A1 | | 5/2010 | Zhe et al. |
| 2010/0295138 A1 | | 11/2010 | Montanya Silvestre et al. |
| 2011/0030472 A1 | * | 2/2011 | Aziz .................. G01P 15/0802 |
| | | | 216/13 |
| 2011/0048133 A1 | | 3/2011 | Lin et al. |
| 2011/0054345 A1 | | 3/2011 | Nagatani |
| 2011/0056294 A1 | | 3/2011 | Simoni et al. |
| 2011/0062820 A1 | | 3/2011 | Aoyagi et al. |
| 2012/0272711 A1 | | 11/2012 | Supino et al. |
| 2012/0326700 A1 | | 12/2012 | Swanson et al. |
| 2013/0324832 A1 | | 12/2013 | Wu et al. |
| 2014/0023999 A1 | | 1/2014 | Greder |
| 2014/0125325 A1 | | 5/2014 | Ocak et al. |
| 2014/0182377 A1 | | 7/2014 | Lin et al. |
| 2014/0308757 A1 | | 10/2014 | Ju |
| 2014/0316188 A1 | | 10/2014 | Peterchev et al. |
| 2014/0358016 A1 | | 12/2014 | Shapira et al. |
| 2014/0375338 A2 | | 12/2014 | Chi et al. |
| 2015/0226762 A1 | | 8/2015 | Seshia et al. |
| 2016/0007872 A1 | * | 1/2016 | Bishay ................ A61B 5/0205 |
| | | | 600/382 |
| 2016/0023002 A1 | | 1/2016 | Schulhauser et al. |
| 2016/0081577 A1 | | 3/2016 | Sridhar et al. |
| 2016/0116499 A1 | | 4/2016 | Thompson |
| 2016/0120432 A1 | | 5/2016 | Sridhar et al. |
| 2016/0341762 A1 | | 11/2016 | Waters et al. |
| 2016/0349283 A1 | | 12/2016 | Bramhavar et al. |
| 2017/0097382 A1 | | 4/2017 | Bickford et al. |
| 2017/0097394 A1 | | 4/2017 | Bickford et al. |
| 2017/0164878 A1 | * | 6/2017 | Connor .................. G09B 19/00 |
| 2017/0276697 A1 | | 9/2017 | Campsie et al. |
| 2017/0281086 A1 | | 10/2017 | Donaldson |
| 2018/0284175 A1 | | 10/2018 | Bickford et al. |
| 2018/0292470 A1 | | 10/2018 | Bickford et al. |
| 2020/0025840 A1 | | 1/2020 | Bickford |

FOREIGN PATENT DOCUMENTS

| | | |
|---|---|---|
| CN | 103342562 B | 2/2015 |
| CN | 104459351 A | 3/2015 |
| CN | 205620559 U | 10/2016 |
| CN | 106093605 A | 11/2016 |
| DE | 102014204721 A1 | 9/2015 |
| EP | 0702981 A1 | 3/1996 |
| EP | 2199741 A2 | 6/2010 |
| EP | 2466257 A1 | 6/2012 |
| JP | 2011136158 A | 7/2011 |
| WO | 02084315 A1 | 10/2002 |
| WO | 2012071545 A1 | 5/2012 |
| WO | 2014025353 A1 | 2/2014 |
| WO | 2014205356 A2 | 12/2014 |

OTHER PUBLICATIONS

Williams et al., "Vacuum Steered-Electron Electric-Field Sensor", Journal of Microelectromechanical Systems, pp. 1-10, Jan. 15, 2013.

Ando et al., "E-Field Ferroelectric Sensor: Modeling and Simulation", IEEE Instrumentation & Measurement Magazine, pp. 31-37, 2009.

Bai et al., "A novel easy-driving and easy-signal processing electrostatic field sensor based on piezoresistance and PET lever", Author Submitted Manuscript, pp. 1-15.

Bogue, R., "Plessey launches range of unique electric field sensors", Sensor Review, vol. 32, No. 3, pp. 194-198, 2012.

Chen et al., "Micromachined ac/dc electric field sensor with modulated sensitivity", Sensors and Actuators, No. 245, pp. 76-84, Apr. 26, 2016.

Huang et al., "A novel high-sensitivity electrostatic biased electric field sensor", Journal of Micromechanics and Microengineering, vol. 25, pp. 1-9, Aug. 17, 2015.

Miles et al., "Report on Non-Contact DC Electric Field Sensors", Jun. 23, 2009.

Datskos et al., "Using Micro-Electro-Mechanical Systems (MEMS) as Small Antennas", IEEE, 2012.

Toney et al., "Detection of Energized Structures with an Electro-Optic Electric Field Sensor", IEEE, pp. 1364-1369, May 2014.

Petrov et al., "Electric Field Encephalography as a Tool for Functional Brain Research: A Modeling Study", PLoS One, vol. 8, No. 7, Jul. 3, 2013.

International Search Report and Written Opinion for application No. PCT/US2016/055584 dated Jul. 27, 2017.

Angelakis et al., "EEG Neurofeedback: A Brief Overview and an Example of Peak Alpha Frequency Training for Cognitive Enhancement in the Elderly", The Clinical Neuropsychologist, vol. 21, pp. 110-129, Feb. 16, 2007.

Ashrafulla, S., "EEG and MEG: functional brain imaging with high temporal resolution", Jun. 2013, <URL: https://ngp.usc.edu/files/2013/06/Syed_EEG_MEG.pdf>.

Basar et al., "A review of brain oscillations in cognitive disorders and the role of neurotransmitters", Brain Research, vol. 1235, pp. 172-193, Jul. 2, 2008.

(56) References Cited

OTHER PUBLICATIONS

Bernstein, J., R. Miller, W. Kelley, and P. Ward, "Low-Noise MEMS Vibration Sensor for Geophysical Applications," Journal of Microelectromechanical Systems, val. 8, No. 4, pp. 433-438, 2009.
Choi, K., "Electroencephalography (EEG) based neurofeedback training for brain-computer interface (BCI)", pp. 1-26, Sep. 2013.
Dilella, D., L.J. Whitman, R.J. Colton, T.W. Kenny, W.J. Kaiser, E.G. Vote, J.A. Podosek, L.M. Miller, "A Micromachined Magnetic-Field Sensor Based on an Electron Tunneling Displacement Transducer," Sensors and Actuators. vol. 86, pp. 8-20, 2000.
Dong, S., J. Zhai, F. Bai, J.-F. Li, D. Viehland, "Push-Pull Mode Magnetostrictive/Piezoelectric Laminate Composite with an Enhanced Magnetoelectric Voltage Coefficient," Applied Physics Letters, vol. 87, pp. 62502. 2005.
Gabrielson, T.B., "Mechanical-Thermal Noise in Micromachined Acoustic and Vibration Sensors", IEEE Transactions On Electron Devices, vol. 40, No. 5, pp. 903-909, May 1993.
Grummett et al., "Measurement of neural signals from inexpensive, wireless and dry EEG systems", Physiological Measurement, vol. 36, pp. 1469-1484, 2015.
Heintzelman et al., "Characterization and Analysis of Electric-field Sensors", IEEE, Dec. 17, 2015.
Kingsley et al., "Photrodes for physiological sensing", SPIE 5317, Optical Fibers and Sensors for Medical Applications IV, Jun. 2004.
Kyynarainen, J., J. Saarilahti, H. Katielus, A. Karkkainen, T. Meinander, A. Oja, P. Pekko, H. Seppa, M. Suhonen, H. Kuisma, S. Ruotsalainen, M. Tilli, "A 3D Micromechanical Compass," Sensors and Actuators A, vol. 142, pp. 561-568. 2008.
Latorre, L., V. Beroulle, Y. Bertrand, P. Nouet, and I. Salesse, "Micromachined CMOS Magnetic Field Sensor with Ferromagnetic Actuation," Proceedings of SPIE, vol. 4019, 2000.
Niv, S., "Clinical efficacy and potential mechanisms of neurofeedback", Personality and Individual Differences, vol. 54, pp. 676-686, Jan. 24, 2013.
Othmer, S., "Neuromodulation technologies: An attempt at classification", Introduction to Quantitative EEG and Neurofeedback: Advanced Theory and Applications, second edition, pp. 1-27, 2009.
Prance, H., "Sensor Developments for Electrophysiological Monitoring in Healthcare", Applied Biomedical Engineering, pp. 265-286, Aug. 2011.
Schalk et al., "Brain Sensors and Signals", A Practical Guide to Brain-Computer Interfacing with General-Purpose Software for Brain-Computer Interface Research, Data Acquisition, Stimulus Presentation, and Brain Monitoring, pp. 9-35, 2010.
Stikic et al., "Modeling temporal sequences of cognitive state changes based on a combination of EEG-engagement, EEG-workload, and heart rate metrics", Frontiers in Neuroscience, vol. 8, article 342, pp. 1-14, Nov. 2014.
Tatarchuk, J. J., C. B. Stevens, and R.N. Dean, "A MEMS DC Current Sensor Utilizing Neodymium Rare Earth Magnets," Additional Conferences (Device Packaging, HiTEC, HiTEN, & CICMT): Jan. 2014, vol. 2014, No. DPC, pp. 001046-001071.
Vasquez, D., and J. Judy, "Optically-Interrogated Zero-Power MEMS Magnetometer", Journal of Microelectromechanical Systems, vol. 16, No. 2, pp. 336-343, Apr. 2007.
Wickenden, W., J.L. Champion, R.B. Givens, T.J. Kistenmacher, J.L. Lamb, and R. Osiander, "Polysilicon Xylophone Bar Magnetometers," SPIE vol. 3876, pp. 267-273. Sep. 1999.
Yang, H.H., NV. Myung, J. Yee, D.-Y. Park, B.-Y. Yoo, M. Schwartz, K. Nobe, and J.W. Judy, "Ferromagnetic Micromechanical Magnetometer," Sensors and Actuators A, vol. 97-98, pp. 88-97, 2002.
Zhao, P., Z. Zhao, D. Hunter, R. Suchoski, C. Gao, S. Mathews, M. Wuttig, I. Takeuchi, "Fabrication and Characterization of All-Thin-Film Magnetoelectric Sensors," Applied Physics Letters, vol. 94, p. 243507. 2009.
International Search Report and Written Opinion for application No. PCT/US2016/055567 dated Aug. 31, 2017.
Budzynski et al., "Introduction to Quantitative EEG and Neurofeedback: Advanced Theory and Applications," 2nd ed., Elsevier (2009), chapters 1, 6, 8 and 16.
International Search Report and Written Opinion for application No. PCT/US2017/054461 dated Jan. 18, 2018.
Denison et al., "A Self-Resonant MEMS-Based Electrometer", IEEE Instrumentation and Measurement Technology Conference Proceedings, May 2007, pp. 1-5.
Bickford, J. "Monitoring Brain Activity (E-Field Sensor)", Draper, accessed Oct. 31. 2016.
Kelly et al., "Progress Toward Forecasting of Space Weather Effects on UHF Satcom after Operation Anaconda", Space Weather, Sep. 12, 2014, doi: 10.1002/2014SW001081.
International Search Report and Written Opinion in application No. PCT/US2018/02556 dated Jul. 30, 2018.
Chen et al. "MEM Electric Field Sensor using Force Deflection with Capacitance Interrogation", Power & Energy Society General Meeting. IEEE (2013).
Kuriyama et al. "Electrostatic Field Distribution Measurement Using Silicon Micro-mirror Array", IEEE International Symposium on Electromagnetic Compatibility (2012), pp. 351-356.
Goel, M. "Electret sensors, filters and MEMS devices: New challenges in materials research", Current Science (2003) vol. 85, No. 4, pp. 443-453.
International Search Report and Written Opinion in application No. PCT/US2018/025881 dated Jul. 16, 2018.

\* cited by examiner

MINIATURE ELECTRIC FIELD DETECTOR

CROSS-REFERENCE TO RELATED APPLICATION

This application claims priority under 35 U.S.C. § 119(e) to U.S. Provisional Application Ser. No. 62/819,222, titled "ENHANCED DIAGNOSTICS USING 3D CARDIAC SENSING WITHOUT ELECTRODES AND LEADS," filed on Mar. 15, 2019, which is hereby incorporated herein by reference in its entirety.

BACKGROUND

The human body generates static and time-varying electromagnetic fields which may be measured and used in numerous applications. However, these fields are often faint, even in close proximity to the body, and attenuate as the distance from the human body is increased. For example, ionic currents within muscles of the human body, such as the heart and skeletal muscles (for example, calves, quadriceps, and so forth), will generate voltage fluctuations and magnetic fields during synaptic transmission. While these fields have proven challenging to accurately measure, some approaches exist for directly detecting the electrical activity produced by the body. For example, to determine electromagnetic activity of a patient's heart, numerous electrodes are arranged to measure scalar potential differences across a patient's chest with an electrocardiogram (ECG). A vectorcardiogram (VCG), which may be generated based on multiple ECG measurements, is a 3D vector representation of the patient's heart's electric field, estimated based on the ECG measurements. Electromagnetic activity of the patient's heart may be determined based on the VCG.

SUMMARY

Aspects and examples discussed herein include a sensor system comprising a first substrate configured to be coupled to a user, an electric field detector to detect an electric field generated by the user, the electric field detector being coupled to the first substrate and comprising a second substrate, a proof mass positioned above the second substrate, one or more electrodes coupled to the second substrate, and a control circuit coupled to the one or more electrodes, the control circuit being configured to determine a respective change in capacitance between the proof mass and each respective electrode of the one or more electrodes responsive to torsional movement of the proof mass in response to the electric field, and a controller coupled to the first substrate and to the electric field detector, the controller being configured to receive, from the electric field detector, information indicative of each respective change in capacitance between the proof mass and each respective electrode of the one or more electrodes, and determine, based on the information indicative of each respective change in capacitance between the proof mass and each respective electrode, characteristics of the electric field in at least two dimensions.

In some examples, the electric field detector is removably coupled to the first substrate. In various examples, the system further comprises an adhesive coupled to the first substrate, the first substrate being configured to be removably coupled to the user. In at least one example, the sensor system further comprises an electric dipole coupled to the proof mass, the electric dipole being polarized along a polarization axis. In some examples, the proof mass is configured to rotate about a first torque axis orthogonal to the polarization axis responsive to the electric field having a first vector component aligned with a first electric field axis, the first electric field axis being orthogonal to the polarization axis and the first torque axis, and rotate about a second torque axis orthogonal to the polarization axis responsive to the electric field having a second vector component aligned with a second electric field axis, the second electric field axis being orthogonal to the polarization axis and the second torque axis, wherein the second torque axis is parallel to the first electric field axis and the first torque axis is parallel to the second electric field axis.

In various examples, the one or more electrodes includes a first set of one or more electrodes and a second set of one or more electrodes, the control circuit being configured to determine a first change in capacitance between the proof mass and the first set of one or more electrodes responsive to torsional movement of the proof mass about the first torque axis, and determine a second change in capacitance between the proof mass and the second set of one or more electrodes responsive to torsional movement of the proof mass about the second torque axis. In at least one example, the controller is further configured to determine, based on the first change in capacitance and the second change in capacitance, characteristics of the electric field along the first electric field axis and the second electric field axis.

In some examples, the electric dipole includes a dielectric material, and wherein the control circuit is configured to selectively polarize the dielectric material along a first polarization axis and a second polarization axis, the first polarization axis being orthogonal to the second polarization axis. In at least one example, the proof mass is configured to rotate about a first torque axis orthogonal to the first polarization axis responsive to receiving the electric field along a first electric field axis, the first electric field axis being orthogonal to the first polarization axis and the first torque axis, rotate about a second torque axis orthogonal to the first polarization axis responsive to receiving the electric field along a second electric field axis, the second electric field axis being orthogonal to the first polarization axis and the second torque axis, and rotate about a third torque axis orthogonal to the second polarization axis responsive to receiving the electric field along a third electric field axis, the third electric field axis being orthogonal to the second polarization axis and the third torque axis, wherein the first torque axis is parallel to the second electric field axis and one of the third electric field axis and the second polarization axis, the second torque axis is parallel to the first electric field axis and one of the third electric field axis and the second polarization axis, and the third torque axis is parallel to the first polarization axis.

In at least one example, the one or more electrodes includes a first set of one or more electrodes, a second set of one or more electrodes, and a third set of one or more electrodes, the control circuit being configured to determine a first change in capacitance between the proof mass and the first set of one or more electrodes responsive to torsional movement of the proof mass about the first torque axis, determine a second change in capacitance between the proof mass and the second set of one or more electrodes responsive to torsional movement of the proof mass about the second torque axis, and determine a third change in capacitance between the proof mass and the third set of one or more electrodes responsive to torsional movement of the proof mass about the third torque axis. In some examples, the controller is further configured to determine, based on the first change in capacitance, the second change in capacitance, and the third change in capacitance, characteristics of the electric field along the first electric field axis, the second electric field axis, and the third electric field axis.

In various examples, further comprising a first set of polarization electrodes and a second set of polarization electrodes coupled to the dielectric material, the first set of polarization electrodes being positioned along the first polarization axis and the second set of polarization electrodes being positioned along the second polarization axis. In some examples, the control circuit is configured to generate a first voltage difference across the first set of polarization electrodes to polarize the dielectric material along the first polarization axis, and generate a second voltage difference across the second set of polarization electrodes to polarize the dielectric material along the second polarization axis. In at least one example, generating the first voltage difference includes applying a first voltage to the first set of polarization electrodes at a first frequency, and wherein generating the second voltage difference includes applying a second voltage to the second set of polarization electrodes at a second frequency, the first frequency being different than the second frequency.

In some examples, the electric field detector is configured to detect an electric field generated by a muscle of the user. In various examples, the controller is configured to determine characteristics of an electric field generated by a heart of the user. In at least one example, the controller is configured to determine characteristics of the electric field in three orthogonal dimensions. In some examples, the sensor system further comprises a movement sensor configured to determine information indicative of movement of the electric field detector, the controller being coupled to the movement sensor and being configured to receive the information indicative of the movement of the electric field detector, and determine the characteristics of the electric field based on the information indicative of each respective change in the capacitance between the proof mass and each respective electrode of the one or more electrodes and the information indicative of the movement of the electric field detector. In various examples, determining the characteristics of the electric field based on the information indicative of each respective change in the capacitance between the proof mass and each respective electrode of the one or more electrodes and the information indicative of the movement of the electric field detector includes identifying motion artifacts caused by the movement of the electric field detector.

According to another aspect discussed herein, an electric field detector to detect an electric field generated by a user is provided, the electric field detector comprising a substrate, a proof mass positioned above the substrate, a plurality of electrodes coupled to the substrate, the plurality of electrodes including a first set of one or more electrodes and a second set of one or more electrodes, and a control circuit coupled to the electrode, the control circuit being configured to determine a first change in capacitance between the proof mass and the first set of one or more electrodes responsive to torsional movement of the proof mass about a first torque axis and to determine a second change in capacitance between the proof mass and the second set of one or more electrodes responsive to torsional movement of the proof mass about a second torque axis orthogonal to the first torque axis in response to being exposed to the electric field generated by the user.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Any embodiment disclosed herein may be combined with any other embodiment in any manner consistent with at least one of the objectives, aims, and needs disclosed herein, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. The appearances of such terms herein are not necessarily all referring to the same embodiment. Various aspects, embodiments, and implementations discussed herein may include means for performing any of the recited features or functions.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the disclosure. In the figures, each identical or nearly identical component that is illustrated in various figures is represented by a like numeral. For purposes of clarity, not every component may be labeled in every figure. In the figures.

DETAILED DESCRIPTION

Figure 1:
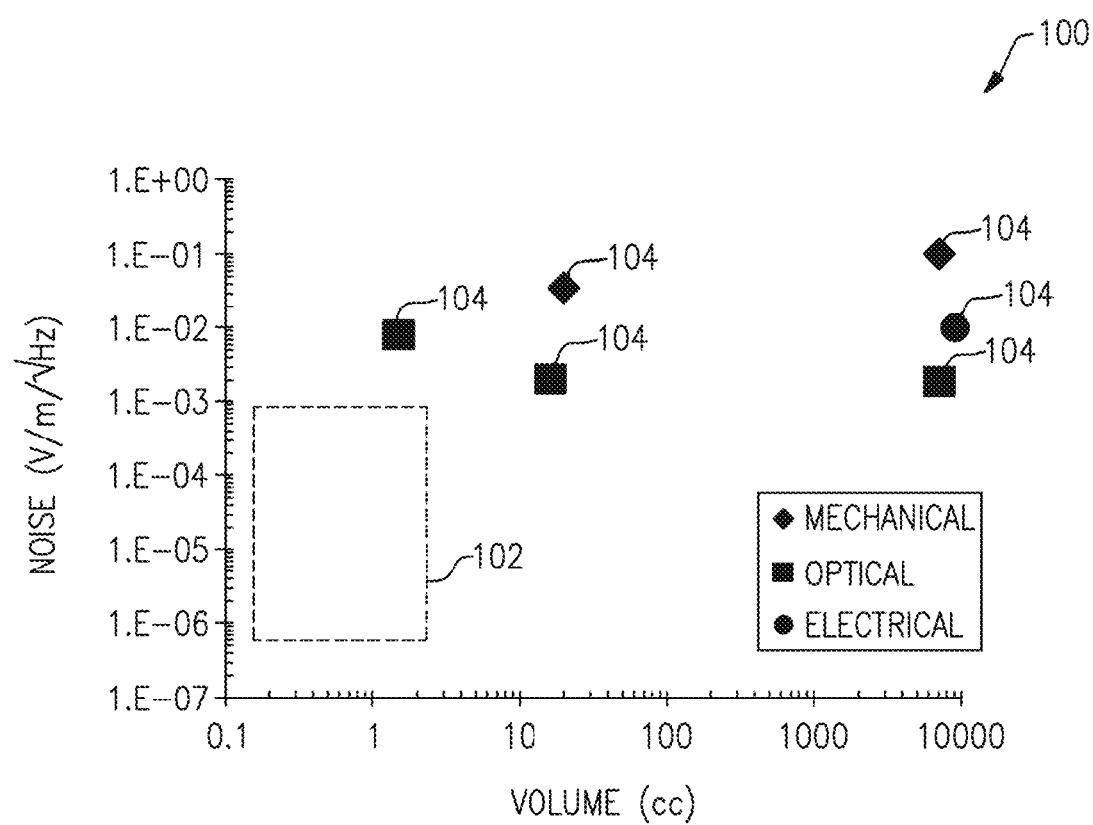
FIG. 1 is a chart showing examples of desirable performance metrics for a compact electric field detector.

Aspects and embodiments are generally directed to detectors for exploiting the electric component of electromagnetic signals. Particular examples may include an electric field detector capable of detecting bio-physical signals generated by the body of a patient or user, such as the electric field of his or her muscles, including the patient's heart or skeletal muscles. Other examples of the electric field detector described herein may be suitable for detecting other weak electromagnetic signals.

In one example, the electric field detector is a microelectromechanical-system-based (MEMS-based) electric field detector which measures one or more torques on a suspended proof mass to determine one or more characteristics of a received electric field. In particular, an electric dipole is generated on the proof mass by placing a quasi-permanently charged material, such as a polymer electret, on the proof mass. In another example, an electric dipole is generated on the proof mass by temporarily charging a dielectric material coupled to the proof mass with an applied voltage along one or more axes, to selectively generate an electric dipole. In either example, the electric dipole generates a torque on the proof mass when exposed to an external electric field in certain dimensions. The torque induces torsional motion in the proof mass, which causes a capacitance between one or more sense electrodes and the proof mass to change. The change in capacitance may then be measured to estimate one or more characteristics of the external electric field, such as a direction, phase, and/or a magnitude. As used herein, "aspects of an electric field," "characteristics of an electric field," "parameters of an electric field," and so forth, may refer to a direction, phase, and/or magnitude of an electric field.

In one example, the electric field detector may be integrated with one or more additional components (including, for example, an energy storage device, a controller, power conditioning circuitry, a communication interface, and so forth) in a single unit capable of determining an electrical field generated by a patient's body. For example, the electric field detector may be integrated into, or removably coupled to, an adhesive patch which can be adhered to a patient's body. Once connected to a patient, the electric field detector may detect an electric field generated by a muscle proximate to the location on the patient's body to which the adhesive patch is adhered. For example, the adhesive patch may be adhered to a patient's chest to detect electrical fields generated by the patient's heart, or may be adhered to a patient's legs to detect electrical fields generated by the patient's calves and/quadriceps, or may be adhered to any other portion of a patient's body to detect electrical fields generated by other muscles. In other examples, the electric field detector may be integrated into another package to be disposed proximate to a patient's body, such as a patient's clothing, a compressive band, a watch band, compressive straps, and so forth. In still other examples, the electric field detector may be integrated into a catheter system or implantable device. For example, the electric field detector may be integrated into a catheter system to measure intracardiac signals produced by a patient's heart.

In some examples, the electric field detector may include multiple elements. For example, the electric field detector may include multiple single-axis elements, each configured to determine characteristics of an electric field in a respective dimension. The multiple single-axis elements may be arranged to measure the strength of an electric field in two orthogonal dimensions or in three orthogonal dimensions. In other examples, the electric field detector may include one or more multi-axis elements, which may be integrated into a monolithic structure, and configured to determine characteristics of an electric field in multiple dimensions, which may be orthogonal dimensions.

One performance metric for sensors configured to detect electrical fields generated by a biological source, such as the heart, brain, or skeletal muscles, includes a noise-performance-versus-volume. For example, various sources have discussed the use of electric field encephalography (EFEG) to estimate brain activity. In particular, some literature has estimated a strength of the relevant bio-electrical signals generated by the brain. Based on the estimated strength of the relevant signals, the performance requirements for an electric field detector capable of detecting these bio-electrical signals can be determined. FIG. 1 illustrates a graph 100 of an example of the performance requirements (for example, noise-performance-versus-volume) for one such electric field detector. In particular, FIG. 1 illustrates these performance requirements (for example, area 102) relative to the performance capabilities of currently available technology (for example points 104). FIG. 1 illustrates that the predicted signal magnitudes of the relevant bio-electrical signals are below the noise floor of current electric field sensors (for example, mechanical, optical, and electrical-based sensors) that could be made compact and inexpensive enough for use in diagnostic applications.

Accordingly, various aspects and examples discussed herein are capable of meeting the performance requirements 102 illustrated in FIG. 1. That is, the electric field detector described herein is capable of directly measuring bio-electrical signals, such as brain activity or muscular activity, with an improvement in signal-to-noise ratio and volume. In some instances, the electric field detector is capable of meeting these performance requirements without contacting the head or body of the given patient or user. Such a design offers the benefit of improved user comfort and convenience. While described herein primarily in the context of bio-electrical signals, it is appreciated that various examples of the electric field detector described herein may also offer significant advantages in other areas of electric field detection.

It is to be appreciated that examples and/or embodiments of the apparatus and methods discussed herein are not limited in application to the details of construction and the arrangement of components set forth in the following description or illustrated in the accompanying drawings. The apparatus and methods are capable of implementation in other embodiments and of being practiced or of being carried out in various ways. Examples of specific implementations are provided herein for illustrative purposes only and are not intended to be limiting. In particular, acts, elements and features discussed in connection with any one or more examples and embodiments are not intended to be excluded from a similar role in any other example or embodiment. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, above and below, and vertical and horizontal are intended for convenience of description, not to limit the present systems and methods or their components to any one positional or spatial orientation.

The accompanying drawings are included to provide illustration and a further understanding of the various aspects and examples, and are incorporated in and constitute a part of this disclosure. The drawings, together with the remainder of the disclosure, serve to explain principles and operations of the described and claimed aspects and examples.

Figure 2A:
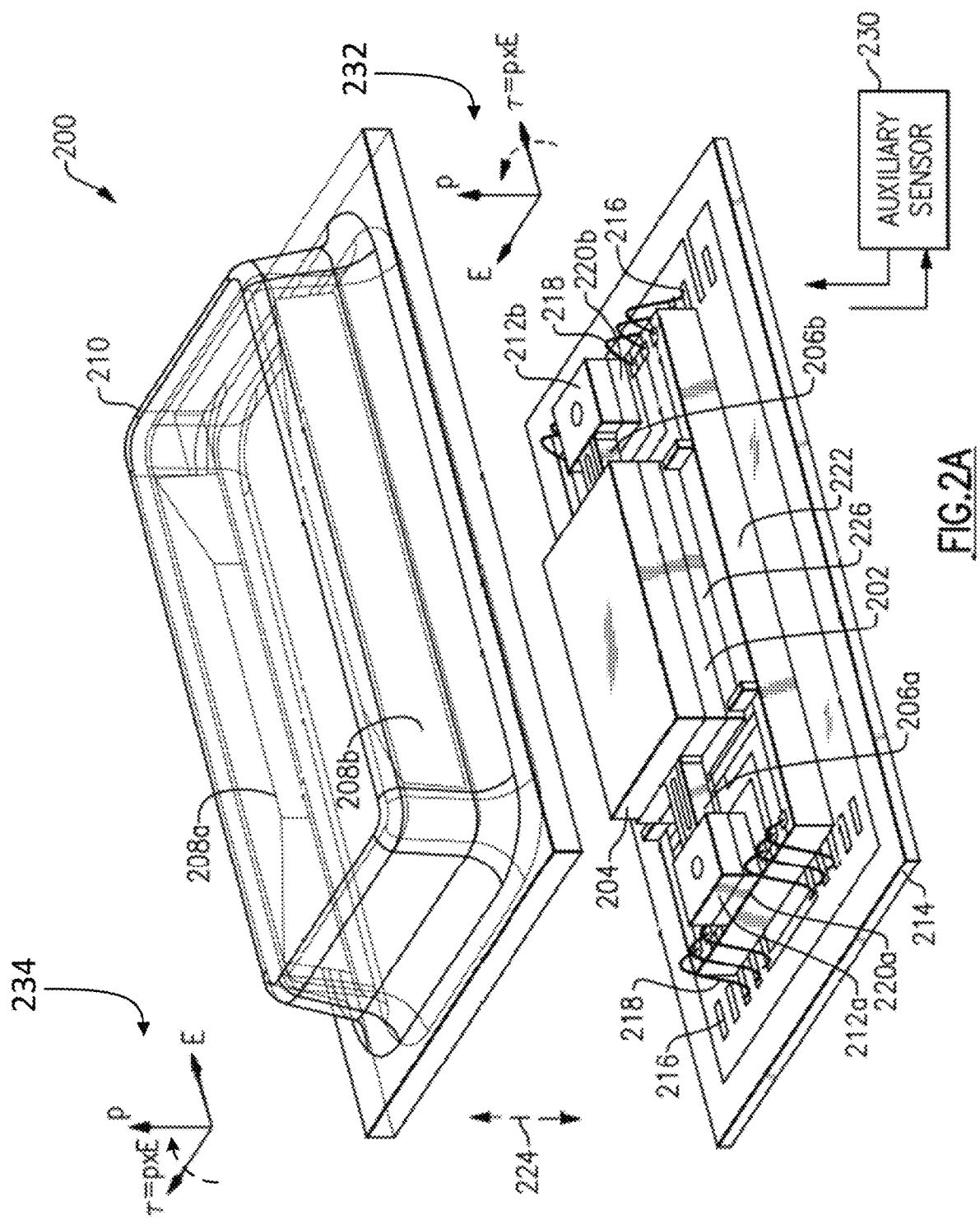
FIG. 2A is a perspective view of an electric field detector, shown with a housing detached from the detector, according to examples discussed herein.
Figure 2B:
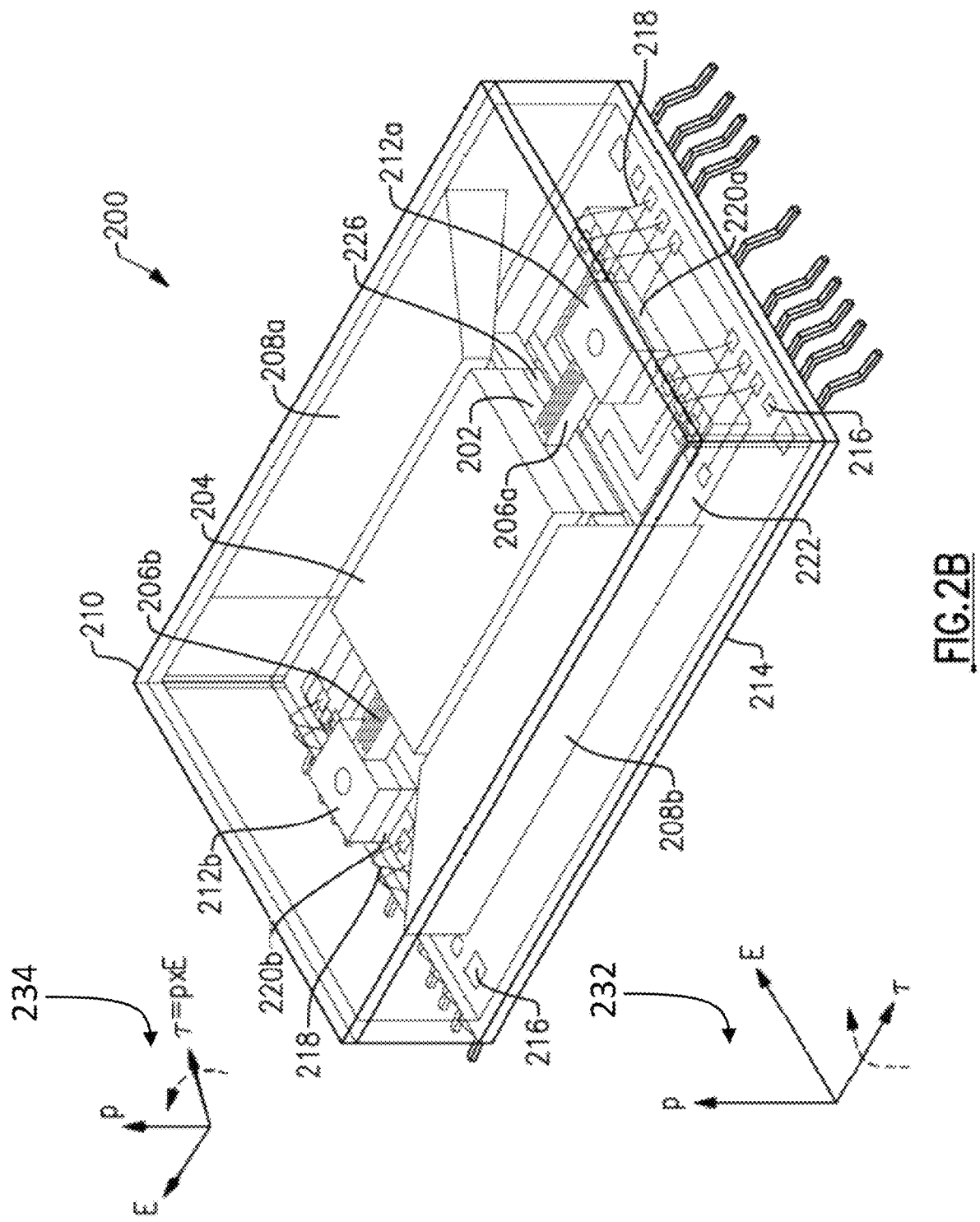
FIG. 2B is perspective view of the electric field detector illustrated in FIG. 2A with the housing attached, according to examples discussed herein.

FIGS. 2A and 2B each illustrate a perspective view of an electric field detector 200 according to various examples described herein. FIG. 2A illustrates a view of the detector 200 with a housing 210 detached from the detector 200, and FIG. 2B shows a view of the detector 200 with the housing 210 attached. The housing 210 may be removed in a vertical direction away from the detector 200 (for example, direction 224), as shown in FIG. 2A. In FIGS. 2A and 2B, the electric field detector 200 includes a MEMS-based resonator, which may be defined by processing a structure wafer (for example, a silicon-on-insulator [SOI] wafer) to a desired geometry. As shown, the detector 200 may include a proof mass 202 coupled to a source of concentrated charge 204, a plurality of supports 206a, 206b (collectively "supports 206"), one or more flux concentrators 208a, 208b (collectively "flux concentrators 208"), the housing 210, one or more anchors 212a, 212b (collectively "anchors 212"), a baseplate 214, one or more electrical contacts 216, one or more leads 218, and a substrate 222, among other components. While not shown in FIGS. 2A and 2B, each of the contacts 216 may couple the electric field detector 200 to a control circuit, examples of which are further discussed herein. In certain examples, the structure wafer is processed (for example, etched) to define the proof mass 202, the plurality of supports 206, and the one or more anchors 212. In further examples, the electric field detector 200 may also include one or more counterbalances 226 that are coupled to the proof mass 202. In certain examples, the electric field detector 200 may also include one or more sense electrodes and one or more drive electrodes, each of which are positioned on the substrate 222 and obscured in FIGS. 2A and 2B by the counterbalance 226. As shown, the substrate 222 is positioned on the baseplate 214

In various examples, the electric field detector 200 determines one or more characteristics of a received electric field, which in one instance is a bio-electrical signal, based on measured capacitance variations due to torsional motion of the proof mass 202 in response to receiving the electric field. While in some examples, a combination of linear forces may result in the torsional motion of the proof mass 202, in certain other examples, a variation in capacitance as a result of a single linear force may be measured. The proof mass 202 is supported by the plurality of supports 206, each of which form a rotationally compliant spring anchored to the substrate 222 via a respective anchor 212a, 212b. In the shown example, each support 206 is a flexured beam interposed between a side surface of the proof mass 202 and a corresponding anchor 212a, 212b. That is, a first support 206a is interposed between a first side surface of the proof mass 202 and a first anchor 212a, and a second support 206b is interposed between a second side surface of the proof mass 202 and a second anchor 212b. Each anchor is coupled to the substrate 222 with a respective anchor ground 220a, 220b. The first anchor 212a is coupled to the substrate 222 at the first anchor ground 220a, and the second anchor 212b is coupled to the substrate 22 at the second anchor ground 220b.

As shown in FIG. 2A, the first support 206a and the second support 206b may be coupled to opposing sides of the proof mass 202. The dimensions of the supports 206 are selected such that the overall stiffness of the supports 206 are sufficient to withstand operational shock loads while maximizing a response to input torques. While shown as including a pair of supports 206a, 206b, in various other examples the electric field detector may include one (for example, in a "lever" arrangement) or any number of supports 206. For instance, the detector 200 may include three supports 206, or an arrangement of four or more supports 206.

In various other examples, the proof mass 202 may be levitated by an electrostatic suspension, levitated by an electromagnetic suspension, and/or suspended by an equivalent rotational bearing. Unlike the example illustrated in FIG. 2A, in these examples it may be advantageous to design the proof mass 202 (and/or source of concentrated charge 204) to have a circular or cylindrical shape to permit rotation thereof. In such an example, the levitated proof mass (for example, relative to a substrate) is positioned to move (for example, rotate) with very low resistance and low stiffness. Such an arrangement may maximize a scale factor of the electric field detector 200 while retaining a structural stability and robustness. In such an example, the electrostatic suspension, electromagnetic suspension, and/or rotational bearing may supplement the one or more illustrated flexured beams of FIG. 1 (for example, supports 206) or replace the one or more flexured beams.

Figure 9:
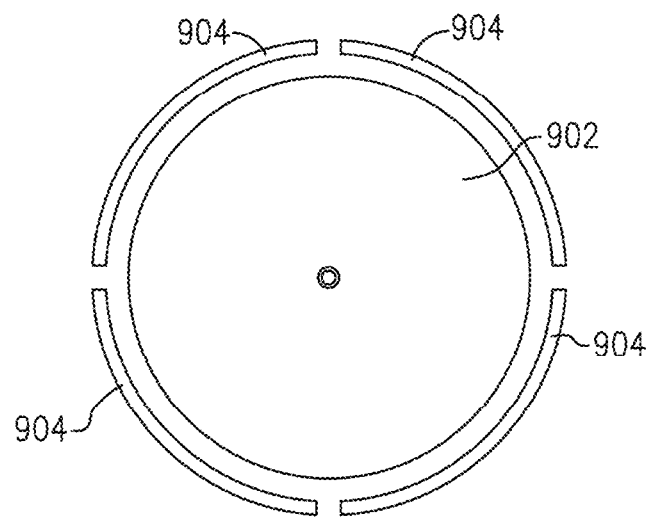
FIG. 9 is an axial view of a proof mass and levitation forcers, according to various examples discussed herein.
Figure 10:
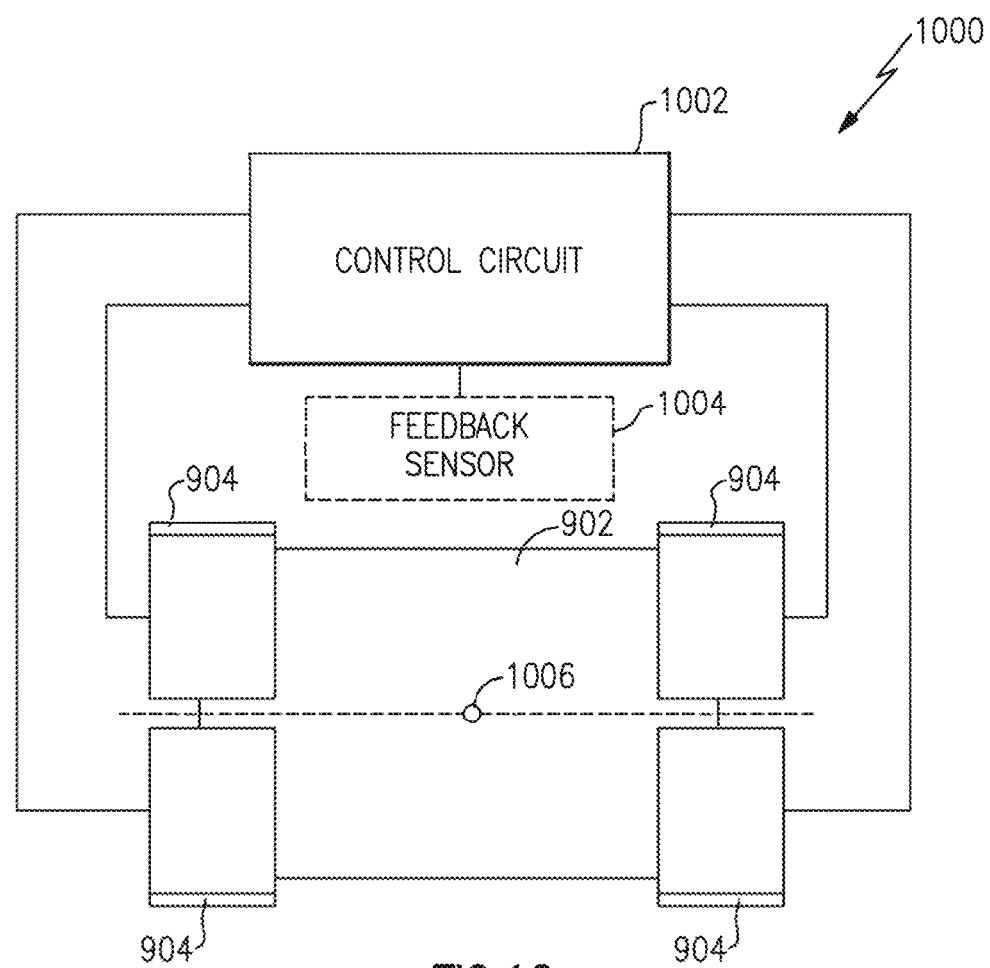
FIG. 10 is a side profile view of a levitation suspension system including the levitation forcers of FIG. 9, according to various examples discussed herein.

One example of a levitation suspension system 1000 is described with reference to FIG. 9 and FIG. 10. In particular, FIG. 9 illustrates an axial view of a proof mass 902 and levitation forcers 904, and FIG. 10 illustrates a profile view of a levitation suspension system 1000 that includes the levitation forcers 904 of FIG. 9. Examples of the levitation suspension system 1000 may be incorporated within any of the examples of the electric field detectors described herein, such as the electric field detector 200 described with reference to FIG. 2A and FIG. 2B. That is, the proof mass 902 may be the proof mass 202 illustrated in FIG. 1. FIG. 9 illustrates an axial view of a proof mass 902 and levitation forcers 904, and FIG. 10 shows a side profile view of the levitation suspension system 1000. As shown, the levitation suspension system 1000 may include one or more levitation forcers 904 that apply a levitating force to the proof mass 902 to levitate the proof mass against gravity and other induced forces. In certain examples, each of the one or more levitation forcers 904 may include one or more sense electrodes 502 or drive electrodes 504 further described below with reference to FIG. 5. While in certain examples, each levitation forcer 904 may be an electrostatic forcer (for example, for electrostatic levitation), in various other examples, each levitation forcer 904 may be a magnetic forcer (for example, for magnetic levitation).

A control circuit 1002 (for example, control circuit 600 illustrated in FIG. 6) coupled to the levitation forcers 904 receives feedback from each levitation forcer 904 and/or one or more feedback sensors 1004. If a position of the proof mass 902 is displaced relative to a desired null point (for example, shown as point 1006), the control circuit 1002 provides a control signal to one or more of the levitation forcers 904 to increase or decrease the force applied by the receiving levitation forcer 904 and return the proof mass 902 to the null position. In certain examples, the proof mass 902 may be metalized (for example, at an end of the proof mass) to increase the sensitivity of the proof mass 902 to the levitation force. The position of the proof mass 902 (relative to the null position) may be capacitively measured based on a capacitance between the proof mass 902 and one or more sense electrodes (for example, sense electrodes 502 described with reference to FIG. 5).

The number and arrangement of levitation forcers 904 may be selected based on the desired application of the corresponding electric field detector. While FIG. 9 illustrates a plurality of levitation forcers 904 (for example, four) radially aligned about the circumference of an axial proof mass 902, various other arrangements are possible. In particular, the number, shape, and arrangement of levitation forcers 904 may depend on the particular shape of the proof mass 902 and packaging constraints (for example, size, weight, available space, etc.). In addition to maintaining the proof mass 902 a desired null position, in certain instances, the levitation forcers 904 may be used to rotate the proof mass 902 at a desired velocity, or reposition the proof mass 902 to a desired orientation. In addition to assessing the position of the proof mass 902 relative to a null position, one or more signals from the illustrated feedback sensor 1004 may be used by the control circuit 1002 to infer external stimuli that induce proof mass 902 movement. The feedback sensor 1004 may be an optical sensor, an accelerometer, a capacitive sensor, or any other type of position sensor.

Referring to FIGS. 2A and 2B, in various examples, the plurality of supports 206 may suspend the proof mass 202 above a substrate offset space defined in the substrate 222. That is, the substrate 222 may include an area (referred to as a "substrate offset space") formed in a surface thereof beneath the proof mass 202 (for example, and counterbalance 226 shown in FIGS. 2A and 2B). The substrate offset space is obscured in FIGS. 2A and 2B by the counterbalance 226. While described as being suspended "above" the substrate offset space, in other examples, the proof mass 222 may be partially positioned within the substrate offset space. In other examples, the proof mass 202 may be positioned in close proximity to the substrate offset space but not directly above the substrate offset space. As discussed, in certain examples, the electric field detector 200 may include one or more sense electrodes and one or more drive electrodes, each of which are positioned on the substrate 222 and in capacitive communication with the proof mass 202. In particular, each of the sense electrodes and the drive electrodes may be positioned within the substrate offset space and may form a sense gap with the proof mass 202. In certain examples, the substrate offset space is formed by etching the substrate 222; however, other processing techniques may be used to form the substrate offset space, such as milling, grinding, or one or more deposition processes. Various aspects of a substrate, a substrate offset space, sense electrodes, and drive electrodes are discussed below with reference to at least FIGS. 7A-7C and FIGS. 8A-8C.

In various examples an impinging electric field concentrated on the source of concentrated charge 204 generates a torque and effects motion of the proof mass 202. For instance, the torque, $\tau$, may be represented as:

$$\tau = p \times E$$

where p is the strength of the electric dipole from the source of concentrated charge 204 (for example, in C-m) and E is the strength of the received electric field (for example, in V/m).

In many instances, the proof mass 202 responds to the torque by rotating about a torque axis. In one example, the rotation can be represented as:

$$\theta = \frac{\tau}{(Is^2) + (Ds) + k}$$

where $\theta$ is the angle of rotation, $\tau$ is the torque, I is the polar moment of inertia, s is the complex frequency, D is a damping coefficient, and k is the rotational stiffness. In this way, the torque generated from the electric field induces motion in the proof mass 202, which reacts against the stiffness of the supports 206 (or the levitation suspension system 1000).

Figure 3:
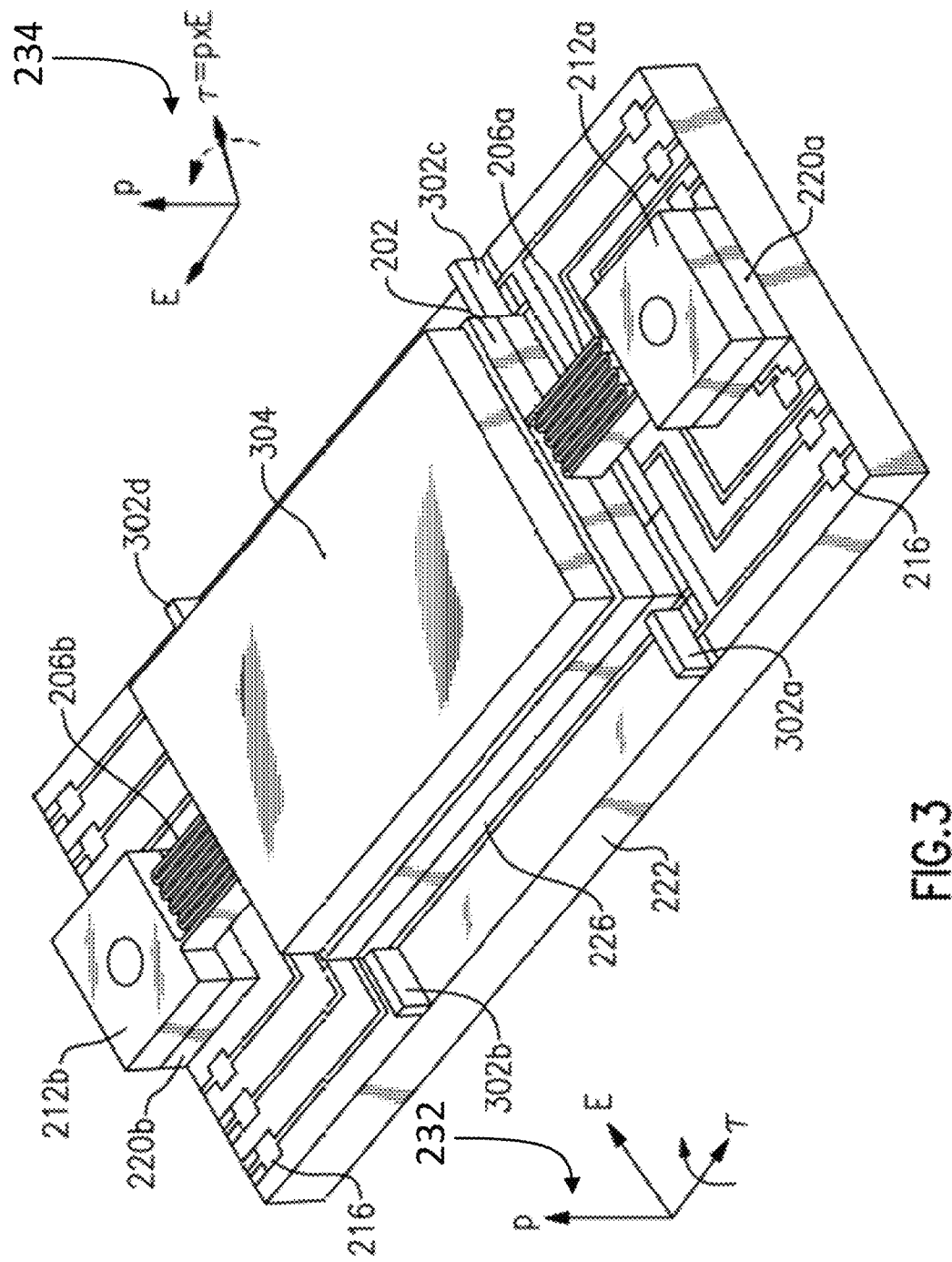
FIG. 3 is another perspective view of components of the electric field detector illustrated in FIG. 2A, according to examples discussed herein.

In some examples, the proof mass 202 may be capable of rotating about multiple torque axes. For example, FIGS. 2A, 2B, and 3 illustrate a first legend 232 and a second legend 234. The legends 232, 234 include a first respective axis, labeled "E," indicating a direction of an external electric field, a second respective axis, labeled "$\tau$," indicating an axis about which the proof mass 202 rotates in response to the external electric field, and a third respective axis, labeled "p," indicating a direction of polarization of the source of concentrated charge 204.

Although the supports 206 may be particularly well-suited for rotating about the torque axis $\tau$ indicated by the first legend 232, the supports 206 may be sufficiently flexible that the proof mass 202 can rotate about the torque axis $\tau$ indicated by the second legend 234 in a manner that can be detected by the electric field detector 200. Accordingly, an electric field may be detected in at least two orthogonal dimensions by the electric field detector 200 in some examples, including the first respective axes in each of the legends 232, 234. Furthermore, it is to be appreciated that the electric field detector 200 may be configured to detect an electric field along a different combination of axes by varying a polarization direction of the source of concentrated charge 204.

In various examples, the rotation of the proof mass 202 increases or decreases the distance between the proof mass 202 and the sense electrode(s) positioned on the substrate 222. In examples in which the electric field detector 200 is configured to detect an electric field in multiple (for example, two) dimensions, there may be multiple sets of one or more sense electrode(s) positioned on the substrate 222, each set being configured to detect increases or decreases in distance between the proof mass 202 and the sense electrode(s) caused by a different component of the electric field. As the distance between the proof mass 202 and the sense electrode(s) increases or decreases, the relative capacitance between the sense electrode(s) and the proof mass 202 varies. The resulting change in capacitance can be measured by the electronics to estimate the characteristics of the received electric field. In various examples, the electric field detector 200 may include a plurality of electrical leads 218, at least one of which couples a sense electrode to a corresponding contact 216. Each electrical contact 216 may connect the corresponding lead 218 to the control circuit, which may determine a direction (or directions), a magnitude, and/or a phase of the received electric field based on the sensed variation in capacitance. For example, the control circuit may determine a direction, magnitude, and/or phase of a received electric field based on the sensed variation in capacitance from a first set of one or more sense electrodes, and may determine a direction, magnitude, and/or phase of the received electric field based on the sensed variation in capacitance from a second set of one or more sense electrodes. As illustrated, the substrate 222 may be coupled to the baseplate 214. Accordingly, the baseplate 214 supports the substrate 222, as well as other components of the detector 200, and may include one or more fasteners for creating a seal with the housing 210.

In certain examples, the control circuit may also send one or more control signals to the electrical contacts 216 and the corresponding leads 218. In particular, the control circuit may generate one or more control signals which can be used charge one or more drive electrodes and produce a feedback torque on the proof mass 202. That is, the electric field detector 200 may further include one or more drive electrodes positioned on the substrate 222 (for example, within the substrate offset space) which rebalance the proof mass 202 to a nominal rotational position based on a received control signal. Such an arrangement may reduce non-linearities in the capacitance measurements (for example, from the supports 206) while also extending the dynamic range of the electric field detector 200. In such an example, a lead 218 may receive the control signal from a contact 216 and provide the control signal to a drive electrode.

In certain examples, the electric field detector 200 may include a source of concentrated charge 204 (for example, concentrated electrical charge). In the example shown in FIG. 2A, the source of concentrated charge 204 is coupled to a top surface of the proof mass 202; however, in certain other examples, the proof mass 202 itself may be composed of charge-concentrated material. That is, a body of the proof mass 202 may be composed of a source of concentrated charge. In various examples, the source of concentrated charge 204 may include any suitable source of a semi-permanent static electric dipole, such as an electret or a capacitor plate having a residual free charge and/or polarization. As will be understood to one of ordinary skill in the art, the term "electret" refers to the dielectric equivalent of a permanent magnet.

For example, an electret configured for use in the detector 200 may be formed by: (a) applying heat to the electret material, (b) in response to obtaining a predetermined temperature, applying a voltage to the electret material, at which point the electret material will act like a capacitor and store the applied charge, and (c) cooling the electret material to a predetermined temperature. Thereafter, the electret maintains a residual charge after the field is removed. As an additional example, the electret material may be bombarded with radiation to generate a residual charge. Accordingly, real surface charges or aligned dipoles are immobilized in the bulk of the dielectric material.

Materials such as polytetrafluoroethylene, silicon nitride, fluorinated ethylene propylene, a perfluoroalkoxy alkane material, Cyptop, cyclotene, and other dielectrics may be suitable materials that can be used as an electret. In certain examples the electret may include, but is not limited to, thermo-electrets, metal-polymer electrets, radio-electrets, and mechanoelectrets. In some examples, the source of concentrated charge 204 may be charged (that is, by applying a voltage thereto) prior to coupling the source of concentrated charge 204 to the proof mass 202. In certain other examples, the source of concentrated charge 204 may be first coupled to the proof mass 202, and then charged. After formation, residual surface potentials can be maintained with no power input since the charge is retained in the source of concentrated charge 204 (for example, in deep traps within the electret material). In some instances, the residual surface potential may be more than 1 kV.

Further examples of the source of concentrated charge 204 may include a series of two or more stacked electrets or a plurality of electrets arranged in a predetermined order. To increase the strength of the electric dipole, and therefore increase the sensitivity of the detector 200 to electric fields, micron-thick layers of electrets may be stacked together. Metal layers may be interposed between one or more layers of the source of concentrated charge 204 (for example, stacked electret layers) to increase the gain of the one of more field concentrators 208 positioned adjacent the proof mass 202. For example, the metal layers of some embodiments may include layers of gold or platinum.

In other examples, the source of concentrated charge 204 may generate a semi-permanent dynamic electric dipole by driving a piezoelectric material (for example, PZT). For instance, the control circuit may continuously, or periodically, drive the PZT to refresh the charge distribution when depleted. In other examples, the control circuit may actively generate a voltage gradient across the proof mass 202 of the electric field detector 200 (or a dielectric material connected thereto) to generate a dynamic electric dipole. In such an example, one or more electrodes or piezoelectric materials may supply an induced voltage (for example, active excitation signal) to vary a dynamic electric dipole at the proof mass 202. Specifically, the electrodes may be driven by the control circuit at an alternating-current (AC) frequency such that the detector 200 up-converts (for example, increases a frequency) the received electric field information to a frequency above a 1/f noise limit, improving the performance of the detector 200. For example, the control circuit may drive the electrodes at an AC frequency that is based on (for example, substantially equal to) a resonant frequency of the proof mass 202.

Figure 11A:
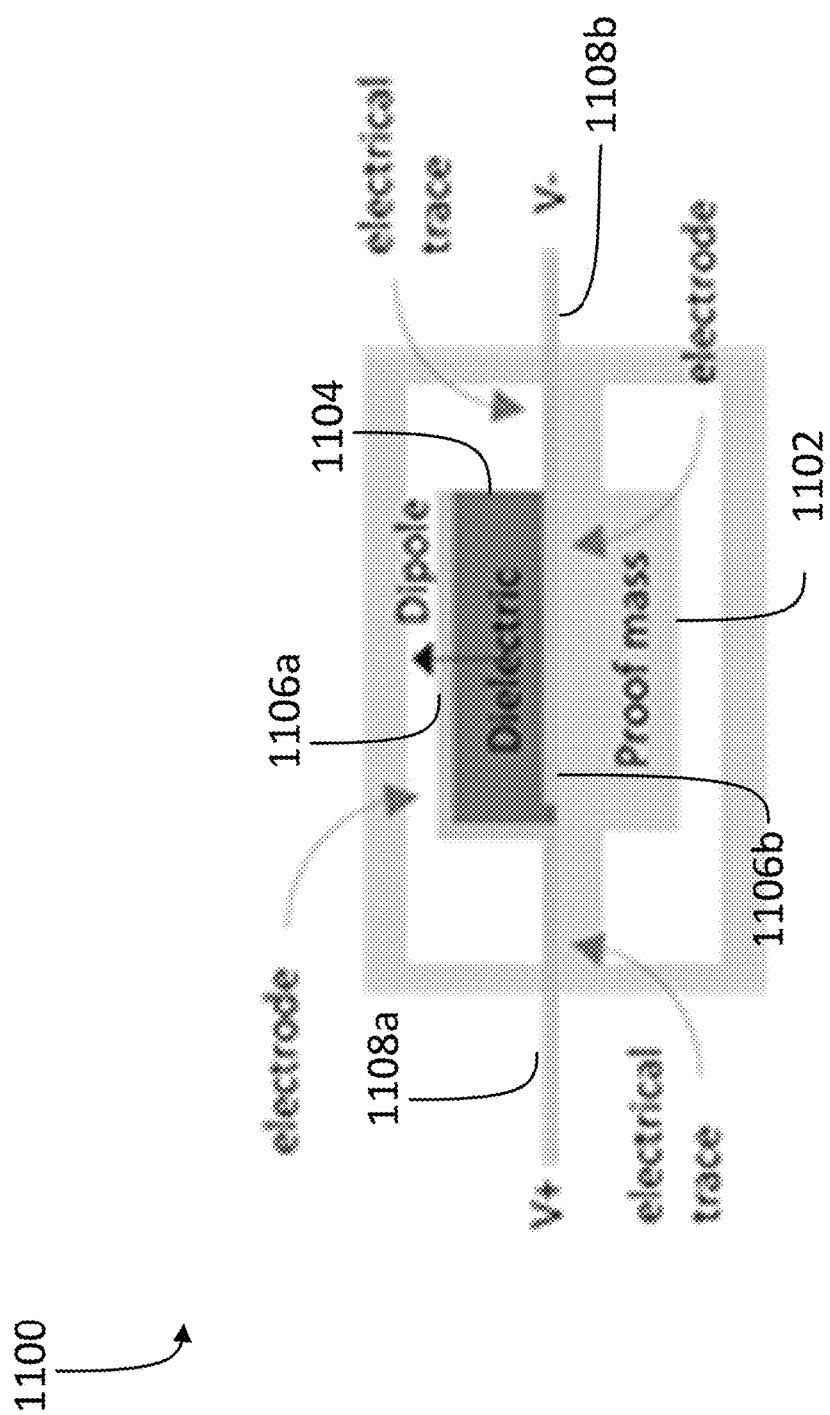
FIG. 11A illustrates a side cross-sectional view of an electric field detector according to an example.
Figure 11B:
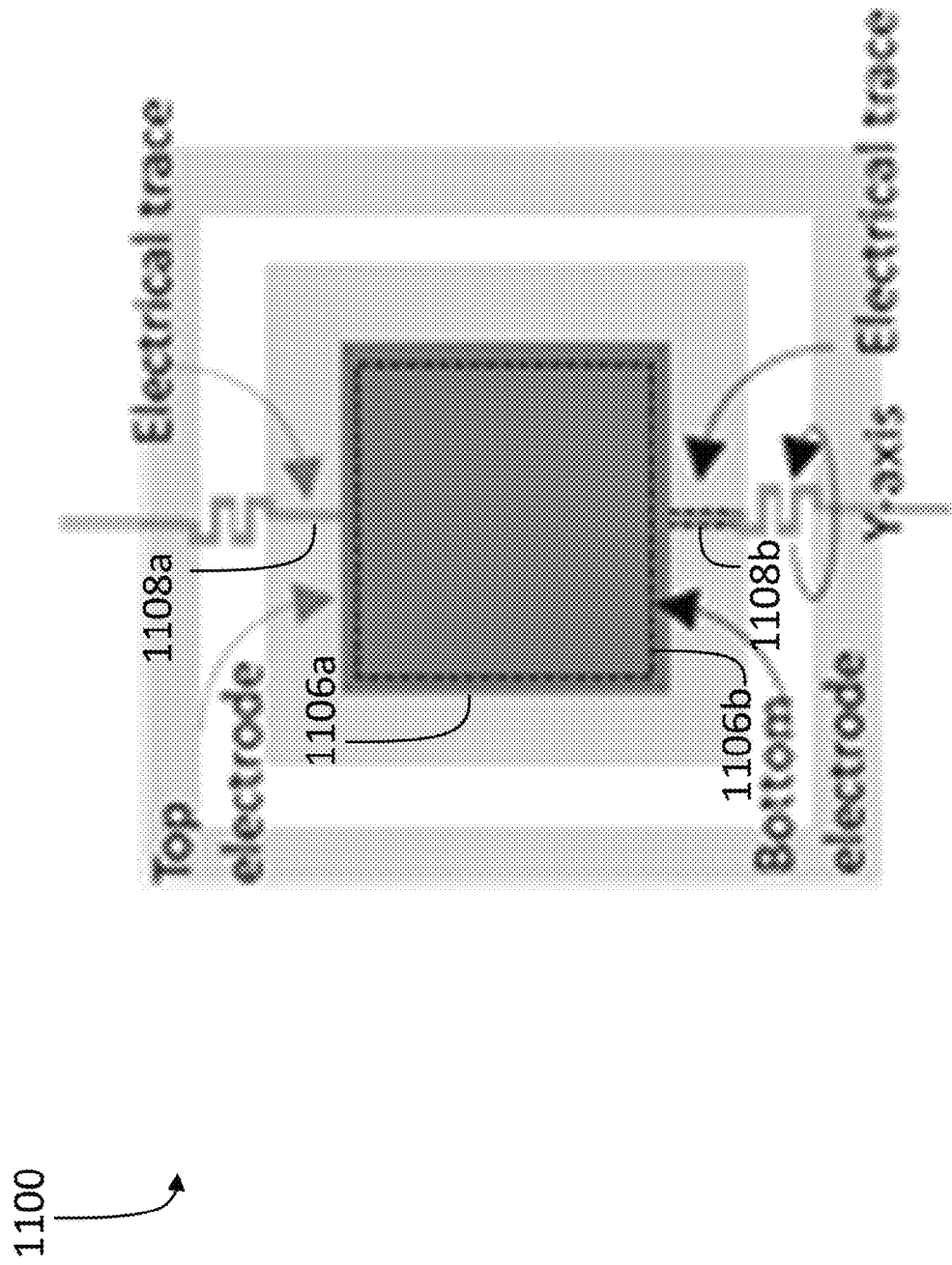
FIG. 11B illustrates a top view of an electric field detector according to an example.

In one example, a dynamic electric dipole is provided by coupling a selectively charged component to the proof mass 202. For example, FIG. 11A illustrates a side cross-sectional view of a portion of an electric field detector 1100 according to an example and FIG. 11B illustrates a top view of a portion of the electric field detector 1100 according to an example. The electric field detector 1100 includes a proof mass 1102, a dielectric component 1104, a first electrode 1106a and a second electrode 1106b (collective, "electrodes 1106"), and a first trace 1108a and a second trace 1108b (collectively, "traces 1108"). The electric field detector 1100 may be substantially similar to the electric field detector 200, except that the dielectric component 1104 provides a dynamic electric dipole in lieu of the source of concentrated charge 204.

The first trace 1108a is coupled to the first electrode 1106a, and is configured to be coupled to a power source. For example, the first trace 1108a may be coupled to a power source configured to provide a positive voltage relative to a reference voltage (for example, ground). The first electrode 1106a is coupled to a first surface of the dielectric component 1104, and is configured to apply a voltage supplied by the power source to the first surface of the dielectric component 1104.

The second trace 1108b is coupled to the second electrode 1106b, and is configured to be coupled to a power source, which may be the same power source or a different power source than that coupled to the first trace 1108a. For example, the second trace 1108b may be coupled to a power source configured to provide a negative voltage relative to the reference voltage. The second electrode 1106b is coupled to a second surface of the dielectric component 1104, which may be an opposite surface from the first surface of the dielectric component 1104, and is configured to apply a voltage (for example, an AC voltage) supplied by the power source to the second surface of the dielectric component 1104.

In one example, where the first trace 1108a applies a positive voltage to the first electrode 1106a from the power source and the second trace 1108b applies a negative voltage to the second electrode 1106b from the power source, a potential difference is generated across the dielectric component 1104. In various examples, the dielectric component 1104 may include a dielectric material or materials such that an electric dipole is generated across the dielectric component 1104. The electric dipole generated by the dielectric component 1104 may be similar to that provided by the source of concentrated charge 204. However, the dielectric component 1104 may be selectively and configurably charged, rather than being substantially fixedly charged. For example, the power source or power sources coupled to the traces 1108 may provide AC power to the electrodes 1106 at a configurable frequency. Moreover, in some examples, the electric field detector 1100 may include several sets of one or more electrodes positioned along various axes of the dielectric component 1104 such that the dielectric component 1104 may be selectively charged along the various axes. That is, although FIGS. 11A and 11B illustrate the electrodes 1106 as being positioned along one axis, in other examples, the electric field detector 1100 may be coupled to electrodes positioned along any of three axes of three-dimensional space such that the electric field detector 1100 may be polarized along any of the three axes of three-dimensional space.

The power source or power sources may drive the electric dipole at a carrier frequency to improve electric field sensitivity within certain bands. For example, the carrier frequency may be tuned to a resonant frequency of the dipole structure (including, for example, the proof mass 1102 and/or the dielectric component 1104) to improve sensitivity at that frequency. In another example, the carrier frequency may be set higher than electric field frequencies of interest (that is, the frequencies of the electric fields generated by a patient) such that the amplified signal of interest may be up-modulated to lower noise frequency bands of the amplifier. The amplified signal of interest may be subsequently demodulated following amplification.

As illustrated in at least FIGS. 2A-2B, in at least one example the proof mass 202, the supports 206, and the anchors 212a, 212b are defined in a same structure wafer. For instance, the structure wafer may include an SOI wafer having a flexure layer, a handle layer, and an oxide layer. The oxide layer may be interposed between the flexure layer and the handle layer. As further described with reference to FIGS. 7A-7C and FIGS. 8A-8C, one example of the proof mass 202, the supports 206, and the anchors 212a, 212b may be defined in the flexure layer. It is appreciated that in some instances, the source of the concentrated charge 204 and/or an intervening material (for example, a glue or other adhesive material) between the source of concentrated charge 204 and the proof mass 202 may introduce an asymmetry in a balance of the proof mass 202. Such an asymmetry may generate undesired sensitivities to external accelerations. In certain particular examples, the electric field detector 200 may include the one or more counterbalances, such as the counterbalance 226, to compensate for asymmetries.

In various examples, the electric field detector 200 may alternatively or additionally compensate for the external accelerations, and/or effects from other external parameters, by directly measuring the external parameter with an auxiliary sensor, and adjusting the measured electric field to compensate for the external parameter. For instance, in addition to external movements and/or accelerations, the auxiliary sensor may measure at least one of noise, ambient temperature, or vibrations. Accordingly, the auxiliary sensor may include an accelerometer, temperature sensor, or noise sensor, to name a few examples. The control circuit may receive measurements from the auxiliary sensor using various filtering techniques (for example, digital signal processing filter techniques), for example, to adjust the characteristic of the electric field to compensate for the effect(s) of the measured external parameter on the measured characteristic of the electric field. In various examples, adjusting the measured characteristic of the electric field may include applying a filter to remove the effect(s) of the external parameter. For example, movement of the electric field detector 200 may cause certain undesirable motion artifacts to appear. By identifying movement of the electric field detector 200 with an auxiliary sensor, such as an accelerometer, optical sensor, or magnetic sensor, these motion artifacts may be identified and eliminated as having been caused by movement of the electric field detector 200. The particular arrangement and position of auxiliary sensors within the electric field detector 200 may vary based on the particular external parameter desired to be measured, as well as the particular architecture of the electric field detector 200 itself. Accordingly, an auxiliary sensor is generally represented by auxiliary sensor block 230 in FIG. 2A (not illustrated in FIG. 2B and FIG. 3).

Referring to FIG. 3, there is illustrated a view of the electric field detector 200 shown in FIGS. 2A and 2B with at least the housing 210 and the baseplate 214 removed. In FIG. 3, a counterbalance 226 is positioned on a bottom surface of the proof mass 202 and also suspended above the substrate offset space. The counterbalance 226 reduces the pedulosity of the proof mass 202 and, therefore, a sensitivity of the proof mass 202 to undesired inputs, such as vibrations. In further examples, mechanical stops 302a, 302b, 302c, 302d may be coupled to the counterbalance 226 to prevent large excursions of the proof mass 202 from a predefined area of travel. That is, the mechanical stops 302a, 302b, 302c, 302d may be positioned to define a limit of travel of the proof mass 202 relative to the substrate 222 and within the detector 200. For example, FIG. 3 shows each of the mechanical stops 302a, 302b, 302c, 302d coupled to a side surface of the counterbalance 226. While shown as having one of the mechanical stops 302a, 302b, 302c, 302d at each corner of the rectangular counterbalance 226, in various other examples, the mechanical stops 302a, 302b, 302c, 302d may be positioned at other locations on the counterbalance 226, or may be attached to the housing 210.

Returning to FIGS. 2A and 2B, the flux concentrators 208 can operate to focus the received electric field on the source of concentrated charge 204. As shown, the flux concentrators 208 may be integrated within the housing 210, and in particular, attached to an interior surface of the housing 210. In other examples, the flux concentrators 208 may be attached to the substrate 222 or the baseplate 214. In various examples, the flux concentrators 208 magnify the intensity of the electric field near the location where the electric field intercepts the source of concentrated charge 204. The flux concentrators 208 may each be composed of metal, or a material with a high dielectric constant, which routes the flux through a spatial volume thereof. For example, each flux concentrator 208 may be composed of copper. By positioning the flux concentrators 208 near the source of concentrated charge 204, the electric field is concentrated to provide a gain at the source of concentrated charge 204. In the shown example, a first flux concentrator 208a is positioned proximate a side surface of the proof mass 202 and a second flux concentrator 208b is positioned proximate another, distal, side surface of the proof mass 202.

In various examples, each flux concentrator 208 is positioned as close as possible to the source of concentrated charge 204 to maximize the provided gain. The performance of each flux concentrator 208 may also be enhanced by increasing a length and/or an area of the respective flux concentrator 208 to maximize the amount of flux received and directed to the source of concentrated charge 204. Relative to the housing 210, each flux concentrator 208 may be internal, external, or a combination of both depending upon the level of enhancement desired. In addition to the flux concentrators 208, in certain examples the electric field detector 200 may include additional signal processing components which enhance the ability of the electric field detector 200 to resolve small signals. Such components are further described below with reference to at least FIG. 6. According to certain other examples, the one or more sense electrodes (or sets of one or more sense electrodes) and the one or more drive electrodes (or sets of one or more drive electrodes) that provide the capacitive readout may be replaced by other structures that are configured to measure the torque or torques on the proof mass 202 from a received electric field. For instance, the electric field detector 200 may include one or more sensors that measure the torque by its effect on a frequency of one or more of the plurality of supports 206, or one or more sensors that optically measure a displacement of the proof mass 202.

In some examples, the electric field detector 200 includes one or more sense electrodes 502 to determine a distance between the proof mass 202 and the one or more sense electrodes 502. Furthermore, in some examples, the electric field detector 200 includes sense electrodes configured to determine torsional movement of the proof mass 202 without a distance between the proof mass 202 and the sense electrodes changing. For example, a capacitance between the proof mass 202 and the sense electrodes may change as a capacitive coupling between the proof mass 202 and the sense electrodes changes due to changes in an overlap between the proof mass 202 and the sense electrodes caused by torsional movement of the proof mass 202. For example, the proof mass 202 and the sense electrodes may collectively include a comb-like structure having elements (for example, silicon-based elements) that slide past one another as the proof mass 202 rotates, thereby causing variations in a capacitance between the proof mass 202 and the sense electrodes sensed by the sense electrodes. Thus, the sense electrodes may sense rotation of the proof mass 202 about all three dimensions of three-dimensional space.

As also shown in FIGS. 2A and 2B, in various examples the electric field detector 200 includes the housing 210. The housing 210 is positioned to encompass the other components of the electric field detector 200, such as the proof mass 202, the plurality of supports 206, the one or more flux concentrators 208, the one or more anchors 212, the substrate 222, the sense electrodes, the drive electrodes, and the one or more electrical contacts 216, among other components. In certain examples, the housing 210 may provide a vacuum environment which reduces the sensitivity of the electric field detector 200 to acoustic coupling and air damping, which reduces Brownian noise. A vacuum environment also helps to ensure that a minimal charge is maintained by preventing the dielectric breakdown of air within the electric field detector 200. In addition to these benefits, the housing 210 protects the discussed components of the electric field detector 200 from dust, moisture, and other contaminants. In one example the housing 210 may be formed from transparent glass to permit displacement of the proof mass 202 to be measured optically.

According to an example, a scale factor of the electric field detector 200 may be increased by using one or more bias voltages to create an electrostatic spring with a negative stiffness relative to the mechanical stiffness of the supports 206. A strong bias voltage on a sense electrode, drive electrode, and/or other electrodes positioned near the proof mass 202 and/or source of concentrated charge 204 generates a force (for example, negative spring force) which is opposite of the mechanical spring force of the supports 206, and thereby decreases the overall stiffness of the MEMS structure. Accordingly, when summed, the negative stiffness reduces the total stiffness of the electric field detector 200 and increases the response of the proof mass 202 to a received electric field. Such an approach provides the benefit of increased performance without the loss of robustness, which would otherwise result if the stiffness of each of support 206 was mechanically reduced. While in certain examples the electric field detector 200 may include additional electronics to create a negative spring by force inputs (for example, a control loop or a magnetic field), application of bias voltages to create an electrostatic spring provides the benefit of low-noise performance and reduced complexity.

Figure 4:
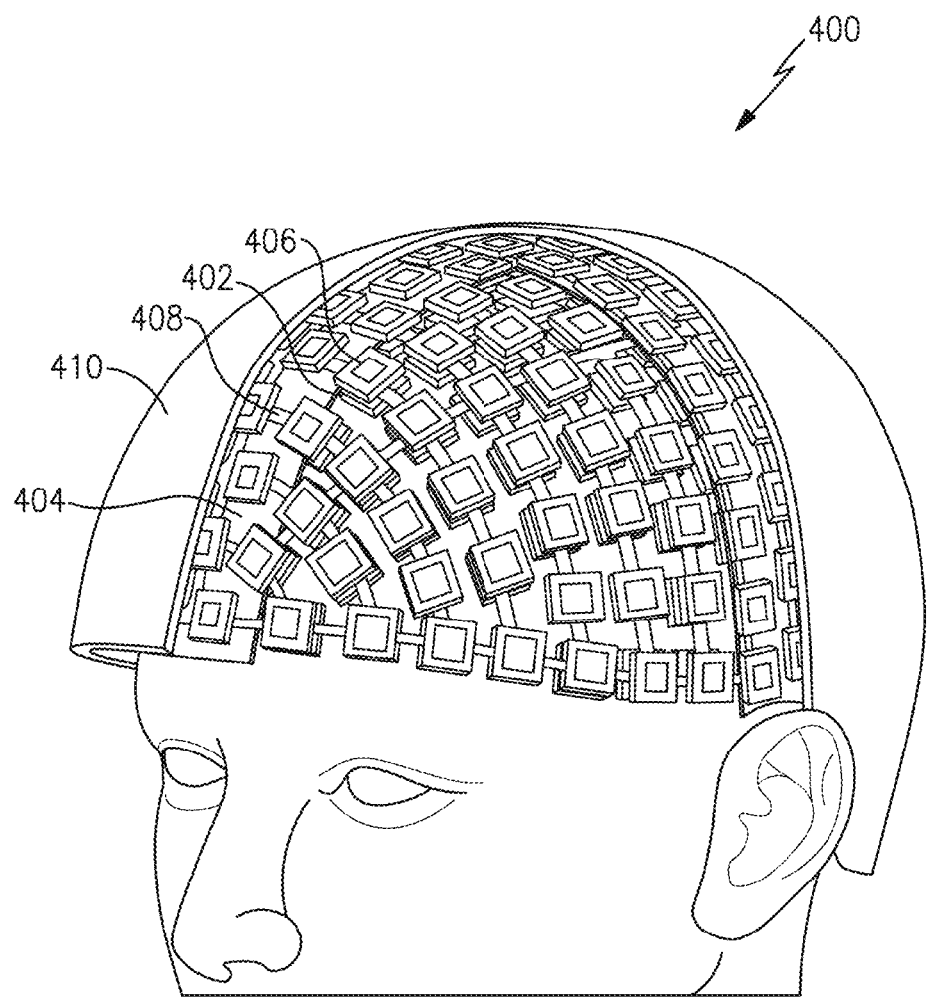
FIG. 4 is a perspective view of an array of electric field detectors incorporated within a headset, according to examples discussed herein.

As discussed herein, multiple electric field detectors 200 may be integrated into an array to enhance electric field detection performance. That is, an array of electric field detectors may be arranged to improve the ability of each individual detector to sense weak electric field signals and/or to measure a spatial distribution of electric fields around the user or patient. FIG. 4 shows one example of an array of electric field detectors incorporated within a headset 400. As shown, the headset 400 may be placed over the head of a patient, or user, to detect bio-electrical signals generated by the brain. It is appreciated that other implementations may be designed to detect bio-physical signals generated by other areas of the body of a patient or user, such as the heart, nerves, or muscles, to name a few examples.

In the example of FIG. 4, each electric field detector 402 within the array is coupled to the other electric field detectors 402 such that received electric field signals are coherently amplified while noise within the array remains incoherent. However, in certain other examples each electric field detector 402 may operate independently to individually measure the amplitude and phase of the received signal.

Referring to FIG. 4, each electric field detector 402 is located between a shield layer 404 (for example, a faraday cage) and the scalp of the patient or user. Each electrical field detector 402 is closely spaced relative to the other electric field detectors 402 (for example, approximately 1 cm apart) to maximize the spatial resolution of the array. On an opposite side of the shield 404 relative to the electric field detectors 402, additional electronics 406 can be positioned. Such an arrangement isolates the electric field detectors 402 from interfering effects which may arise from the operation of the additional electronics 406. For example, the additional electronics may include one or more auxiliary sensors, and/or circuitry for communicating with a control circuit, as discussed below. In this way, the shield 404 isolates the electric field detectors 402 from external noise sources (for example, a 60 Hz power line noise), as well as, system components which may generate interference.

Each of the electric field detectors 402 and additional electronics 406 may be connected to a communication network via an electrical connection 408 that routes measured signals to a central location for processing. Auxiliary sensors may also be incorporated within the electronics 406 of the headset to measure effects which may introduce errors in the intended bio-electrical measurement (for example, one or more external parameters). For example, inertial sensors and/or temperature sensors can be co-located with the electric field detectors 402 to measure electric fields, accelerations (for example, patient movement), or temperature. Likewise, additional sensors, such as blink detectors or other physiological monitors can be incorporated within the headset 400 to improve the accuracy and performance of the array. As shown, components of the headset 400 are embedded within a cap 410 which provides structure and supports the various components. The cap 410 may include padding and other helmet features (for example aesthetically pleasing covers) to increase comfort and improve the user experience.

Accordingly, the array of electric field detectors may provide numerous benefits in various applications. For instance, the array may provide diagnostic information for educational applications, training applications, and cognitive enhancement applications. Moreover, current diagnostic techniques and approaches for neurological conditions may be enhanced by the information ascertained by the array of electric field detectors 402. For instance, the array of electric field detectors 402 enhances current techniques for treating ADHD, autism, dyslexia, depression, insomnia, impulsivity, and anxiety. Other relevant clinical applications include, but are not limited to, pain management, mental health treatment, epilepsy, and dementia, among other brain disorders. In other examples, electric field detectors may be implemented in other applications, including muscle monitoring. For example, electric field detectors may be implemented to monitor electric fields generated by skeletal muscles, such as the calves, quadriceps, and so forth, or other muscles, such as the heart.

Figure 12:
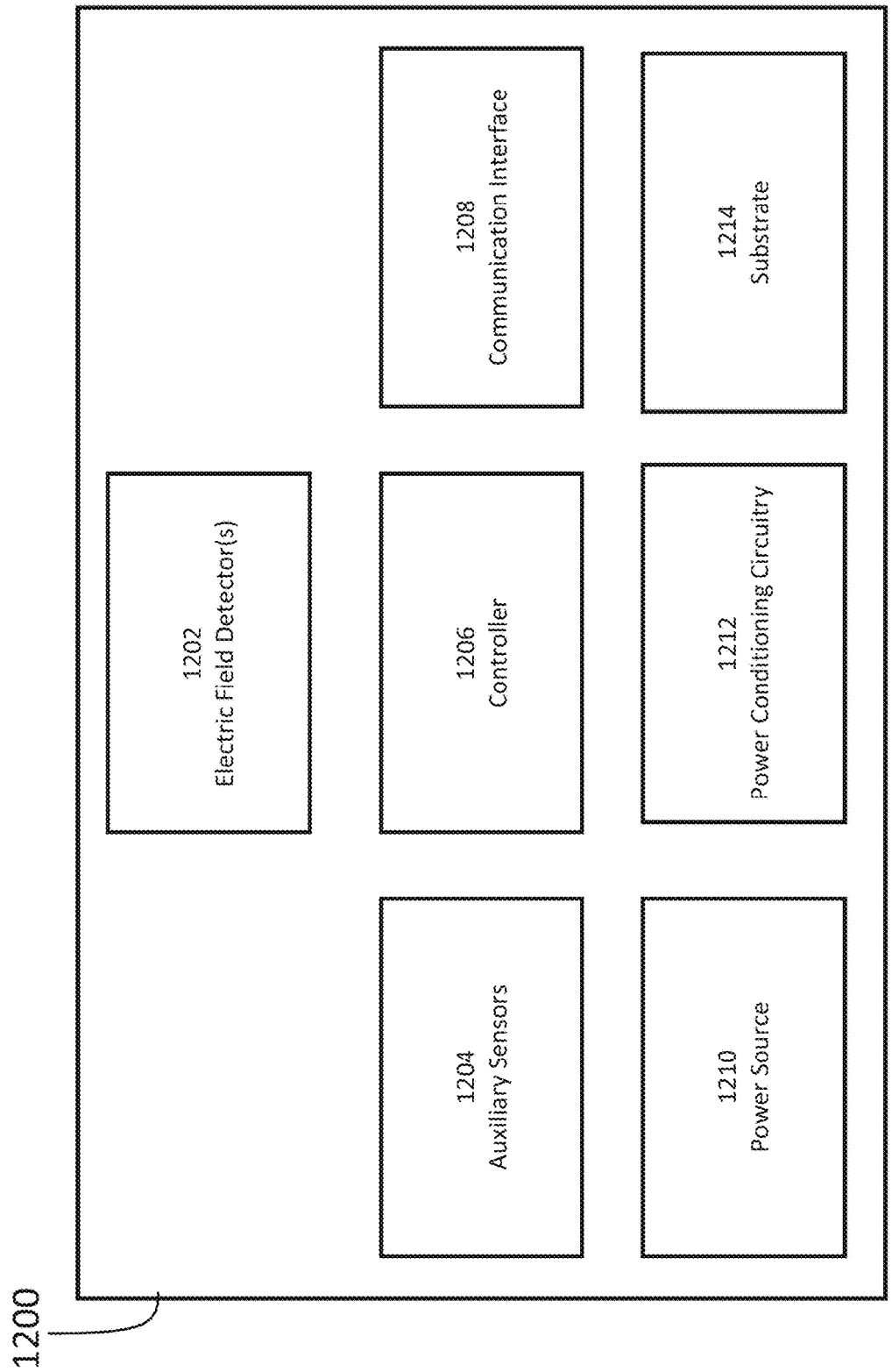
FIG. 12 illustrates a block diagram of a sensor system according to an example.

FIG. 12 illustrates a block diagram of a sensing system 1200 according to an example. The sensing system 1200 may be particularly well-suited to measure biological electric fields, such as those generated by muscles of a patient. The sensing system 1200 includes one or more electric field detectors 1202 (which may include, or be implemented substantially similarly to, the electric field detector 200), one or more auxiliary sensors 1204, a controller 1206, a communication interface 1208, a power source 1210, power conditioning circuitry 1212, and a substrate 1214.

The one or more electric field detectors 1202 are configured to detect parameters of an electric field, such as a direction, phase, and/or magnitude. For example, the one or more electric field detectors 1202 may include electric field detectors substantially similar to the electric field detector 200 and/or the electric field detector 1100. In some examples, the one or more electric field detectors 1202 may include single-axis electric field detectors, as discussed above with respect to the electric field detector 200, and/or may include multi-axis (for example, two- and/or three-axis) electric field detectors configured to detect parameters of an electric field in multiple axes, as discussed in greater detail below. Orientations of the one or more electric field detectors 1202 may be selected to acquire electric field information in a desired number and combination of dimensions. For example, the one or more electric field detectors 1202 may include three orthogonally oriented single-axis electric field detectors to acquire electric field information in all three dimensions of three-dimensional space. In another example, the one or more electric field detectors 1202 may include a single three-axis electric field detector to acquire electric field information in all three dimensions of three-dimensional space. In another example, the one or more electric field detectors 1202 may include two two-axis electric field detectors to acquire electric field information in all three dimensions of three-dimensional space, with redundancy in one dimension. In other examples, the one or more electric field detectors 1202 may include any number of electric field detectors in any combination of orientations. Furthermore, the one or more electric field detectors 1202 may be positioned in various permutations. For example, multiple electric field detectors may be co-located or placed in spatial patterns to improve accuracy and sensitivity by averaging measurements, or by performing inverse modeling to determine spatiotemporal properties of biological signal sources.

The one or more auxiliary sensors 1204 are configured to sense auxiliary information. Similar to the auxiliary sensors 230, the one or more auxiliary sensors 1204 may aid in compensating for external accelerations, and/or effects from other external parameters, by directly measuring the external parameter(s), and adjusting information indicative of a measured electric field to compensate for the external parameter (s). For instance, in addition to external accelerations and/or movements, the one or more auxiliary sensors 1204 may measure at least one of noise, ambient temperature, or vibrations. Accordingly, the one or more auxiliary sensors 1204 may include an accelerometer, gyroscope, magnetometer, temperature sensor, noise sensor, optical sensor, or other sensor, to name a few examples. The controller 1206 may receive measurements from the one or more auxiliary sensors 1204 and use one or more of various filtering techniques (for example, digital signal processing filter techniques), for example, to adjust the characteristic of the electric field sensed by the one or more electric field detectors 1202 to compensate for the effect(s) of the measured external parameter(s) on the measured characteristic of the electric field. In various examples, adjusting the measured characteristic of the electric field may include applying a filter to remove the effect of the external parameter(s). For example, movement of the sensing system 1200 may cause certain undesirable motion artifacts to appear. By identifying movement of the sensing system 1200 with the one or more auxiliary sensors 1204, these motion artifacts may be identified and eliminated as having been caused by movement of the sensing system 1200. The particular arrangement and position of auxiliary sensors within the sensing system 1200 may vary based on the particular external parameter desired to be measured, as well as the particular architecture of the sensing system 1200 itself.

The controller 1206 includes control circuitry to control operation of the sensing system 1200. The controller 1206 may include, or be an example of, a control circuit as discussed herein, and as discussed below with respect to FIG. 6. The controller 1206 is configured to determine, based on information received from the one or more electric field detectors 1202 and/or the one or more auxiliary sensors 1204, characteristics of the electric field as discussed herein. In one example, each of the one or more electric field detectors 1202 includes a control circuit communicatively coupled to the controller 1206 to send information indicative of an electric field. The controller 1206, in turn, may determine characteristics of the electric field based on the received information. The controller 1206 may also be configured to control certain aspects of the one or more electric field detectors 1202. For example, the one or more electric field detectors 1202 may include one or more electric field detectors having a dynamic electric dipole that is selectively polarized at a frequency controlled by the controller 1206 in combination with control circuitry of each respective one of the one or more electric field detectors 1202.

Using data stored in associated memory, the controller 1206 also executes one or more instructions stored on one or more non-transitory computer-readable media that may result in manipulated data. In some examples, the controller 1206 may include one or more processors, field-programmable gate arrays, or other types of controllers. In one example, the controller 1206 is or includes a commercially available, general-purpose processor. In another example, the controller 1206 performs at least a portion of the operations discussed above using an application-specific integrated circuit tailored to perform particular operations in addition to, or in lieu of, a general-purpose processor. As illustrated by these examples, examples in accordance with the present invention may perform the operations described herein using many specific combinations of hardware and software and the invention is not limited to any particular combination of hardware and software components.

The communication interface 1208 is configured to enable communication with one or more external entities. For example, the communication interface 1208 may include an antenna configured to output electromagnetic radiation (for example, radio waves) encoding certain information to an external entity, such as a user device. The controller 1206 may control the communication interface 1208 to output electromagnetic radiation encoding information indicative of parameters of an electric field. For example, the controller 1206 may control the communication interface 1208 to output electromagnetic radiation encoding a direction, magnitude, and/or phase of an electric field produced by a patient's muscles, such as the patient's heart.

The power source 1210 is configured to provide electrical power to components of the sensing system 1200. For example, the power source 1210 may include one or more batteries, which may be rechargeable via a wired or wireless medium.

The power conditioning circuitry 1212 is configured to condition power provided by the power source 1210. Conditioning the power provided by the power source 1210 may include rectifying, inverting, and/or converting power provided by the power source 1210. For example, where the one or more electric field detectors 1202 include a dynamic electric dipole such as the electric field detector 1100, the power conditioning circuitry 1212 and/or the controller 1206 may invert DC power received from the power source 1210 to provide AC power at a desirable frequency to the electrodes 1106. In another example, the power conditioning circuitry 1212 may include one or more power converters configured to step a voltage up or down to a desired level.

The substrate 1214 is configured to couple the sensing system 1200 to a patient. For example, the substrate 1214 may include an adhesive patch having an adhesive side to removably adhere to a patient's body, such as on a patient's chest, legs, arms, and so forth. In another example, the substrate 1214 may include a patient's clothing, including athletic wear (for example, an athlete's padded uniform) and casual wear (for example, a shirt, pants, and so forth). In another example, the substrate 1214 may include a compressive material, such as a band, watch, or strap, to compress around a portion of a patient's body. In other examples, the substrate 1214 may include any other substrate to facilitate coupling of the sensing system 1200 to a patient's body.

The substrate 1214 may fully or partially encapsulate or otherwise include the components 1202-1212. In some examples, the substrate 1214 may be at least partially removable from other components 1202-1212 of the sensing system 1200. For example, the components 1202-1212 may be removably coupled to the substrate 1214 via a removable coupling mechanism such as a snap, a clip, an adhesive, hook-and-loop fastener, a zipper, and so forth. In these examples, the components 1202-1212 may be encapsulated, housed, or otherwise included within another substrate or encapsulate that is configured to be removably coupled to the substrate 1214. Removably coupling the substrate 1214 to the components 1202-1212 may be beneficial where, for example, the substrate 1214 directly contacts a patient's body. It may be undesirable for the substrate 1214 to subsequently directly contact another patient's body, but the components 1202-1212 may still be operational. Thus, the substrate 1214 can be removed and disposed of, and the components 1202-1212 can be coupled to another substrate, substantially similar to the substrate 1214 but not having been previously used with a patient, which may be subsequently coupled to another patient to reduce waste of the components 1202-1212.

In some examples, the sensing system 1200 may be externally coupled to a patient's body. In other examples, the sensing system 1200 may be configured to be inserted into a patient's body. For example, the sensing system 1200 may be, or be included within, an implantable device. In these examples, the substrate 1214 may encapsulate the components 1202-1212 of the sensing system 1200, and may be formed of a biocompatible material or materials that do not adversely affect a patient's body. In another example, the sensing system 1200 may be, or be included within, a catheter (which may be included within an "implantable device"), or other device that is temporarily or removably inserted into a patient's body. In these examples, the substrate 1214 may similarly be formed of a biocompatible material or materials that do not adversely affect a patient's health.

In various examples, the substrate 1214 may include, or be coupled to, a shielding component configured to shield the one or more electric field detectors 1202 from external signals. For example, the substrate 1214 may include, or be coupled to, a metal shielding layer to encapsulate at least a portion of the sensing system 1200 to attenuate or block external electrical fields not generated by the patient from reaching the sensing system 1200. In another example, the substrate 1214 may include a waterproofing material, or may be coupled to a waterproof encapsulate, to prevent moisture from adversely affecting components of the sensing system 1200.

Accordingly, in various examples, components 1202-1212 of the sensing system 1200 may be coupled, contained, or included, removably or non-removably, to or within the substrate 1214. The substrate 1214, in turn, may be coupled to a patient. In other examples, components of a sensing system may be distributed rather than being coupled, contained, or included in a single substrate.

Figure 13:
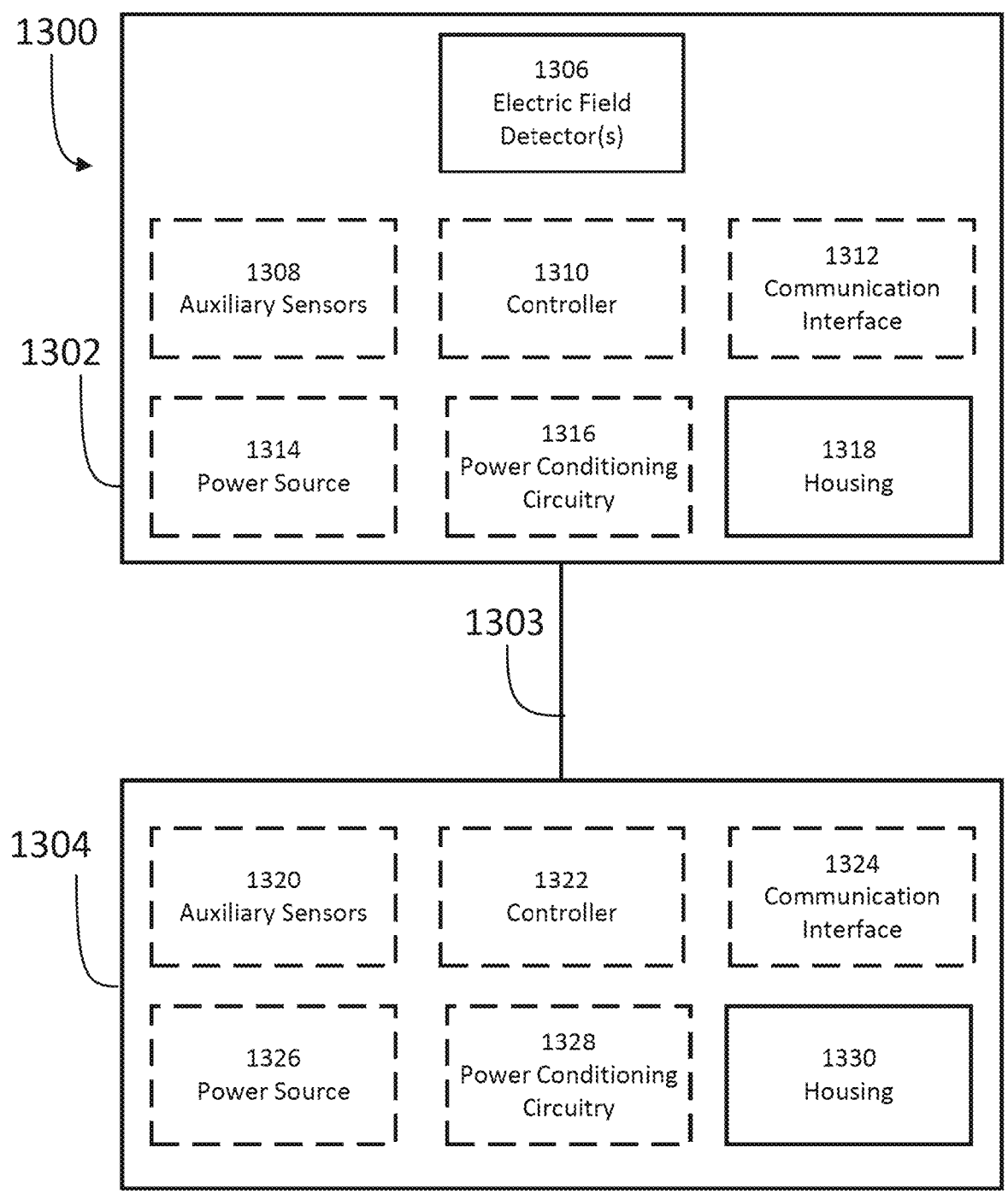
FIG. 13 illustrates a block diagram of a distributed sensor system according to an example.

FIG. 13 illustrates a distributed sensing system 1300 according to another example. The sensing system 1300 may be particularly well-suited to measure internal biological electric fields, such as those generated by a patient. The sensing system 1300 includes an implantable portion 1302, which is configured to be inserted into a patient's body, and an external portion 1304, which is configured to be external to a patient's body. The implantable portion 1302 is communicatively and/or electrically coupled to the external portion 1304 via a connection 1303, which may include wired and/or wireless media. The implantable portion 1302 includes one or more electric field detectors 1306 (which may include, or be implemented substantially similarly as, the electric field detector 200 and/or 1100), and optionally includes one or more first optional auxiliary sensors 1308, a first optional controller 1310, a first optional communication interface 1312, a first optional power source 1314, first optional power conditioning circuitry 1316, and a first housing 1318. The external portion 1304 optionally includes one or more second optional auxiliary sensors 1320, a second optional controller 1322, a second optional communication interface 1324, a second optional power source 1326, second optional power conditioning circuitry 1328, and a second housing 1330.

Components 1308-1316 and 1320-1328 are described as optional components to indicate that the indicated components may be included in either (or both) of the implantable portion 1302 or the external portion 1304. Power and/or information may be exchanged via the connection 1303 depending on which components are included within which of the portions 1302, 1304. For example, where the first optional power source 1314 is included in the implantable portion 1302 and includes an energy source, such as a battery, the first optional power source 1314 may provide power to components of the internal portion 1302. Furthermore, electrical power may be sent from the external portion 1304 via the connection 1303 to charge the first optional power source 1314 and/or provide auxiliary power to other components of the implantable portion 1302 in addition to power provided by the first optional power source 1314. The electrical power may be sent by the second optional power source 1326, which may be included in the external portion 1304 and may include a power source such as a battery, mains utility power, or another power source. Alternatively, the first optional power source 1314 may include a non-rechargeable energy storage device, and the second optional power source 1326 may be omitted completely, or may be included to provide auxiliary power to other components of the implantable portion 1302 in addition to power provided by the first optional power source 1314. In another example, the first optional power source 1314 may not be included in the internal portion 1302, and the second optional power source 1326 may be included in the external portion 1304 to provide electrical power to components of the internal portion 1302 (including, for example, the one or more electric field detectors 1306) via the connection 1303. For example, the second optional power source 1326 may be an external power source, such as an energy storage device (for example, a battery), mains utility power, or another power source.

In another illustrative example, the first optional controller 1310 may be omitted from the implantable portion 1302, the first optional communication interface 1312 may be included in the implantable portion 1302, and the second optional controller 1322 and the second optional communication interface 1324 may be included in the external portion 1304. In this example, information acquired by components of the implantable portion 1302 (for example, the one or more electric field detectors 1306 and/or the first optional auxiliary sensors 1308, if included) may be communicated, from the first optional communication interface 1312 to the second optional communication interface 1324 via the connection 1303, to the second optional controller 1322. For example, the one or more electric field detectors 1306 and/or the first optional auxiliary sensors 1308 may communicate information indicative of electric field information (for example, capacitance information determined by the one or more electric field detectors 1306 and/or movement information, such as acceleration information, determined by the first optional auxiliary sensors 1308) to the second optional controller 1322. The second optional controller 1322 may, in turn, determine electric field information based on the received information. In other examples, the first optional controller 1310 may be included in the implantable portion 1302, and the first optional controller 1310 may determine electrical field information and communicate the electrical field information and/or other information indicative of the electrical field information to the second optional controller 1322, or another entity, via the connection 1303.

Similar principles apply to other optional components of the sensing system 1300, that is, either or both of the implantable portion 1302 and the external portion 1304 may include the optional components depending on an implementation of the sensing system 1300. In various examples, components of the sensing system 1300 may include additional components not specifically identified. For example, where the sensing system 1300 is integrated with a medical device, such as a catheter, the implantable portion 1302 and the connection 1303 may include additional components to enable the traditional functions of the catheter. Furthermore, components of the sensing system 1300 may be adapted for the traditional functions of a medical device in which the sensing system 1300 is integrated. For example, the first housing 1318 and/or the connection 1303 may include a biocompatible material or materials if the first housing 1318 and/or the connection 1303 are to be inserted into a patient's body.

Furthermore, it is to be appreciated that the connection 1303 includes wireless media in some examples. For example, the internal portion 1302 may be an implantable device configured to receive power and/or exchange information with the external portion 1304 via the connection 1303 in a wireless format. For example, the external portion 1304 may provide wireless power to the internal portion 1302 via the connection 1303, and the external portion 1304 may receive information (for example, information indicative of electric field information) via a wireless medium, such as electromagnetic radiation (for example, via radio waves).

Figure 5:
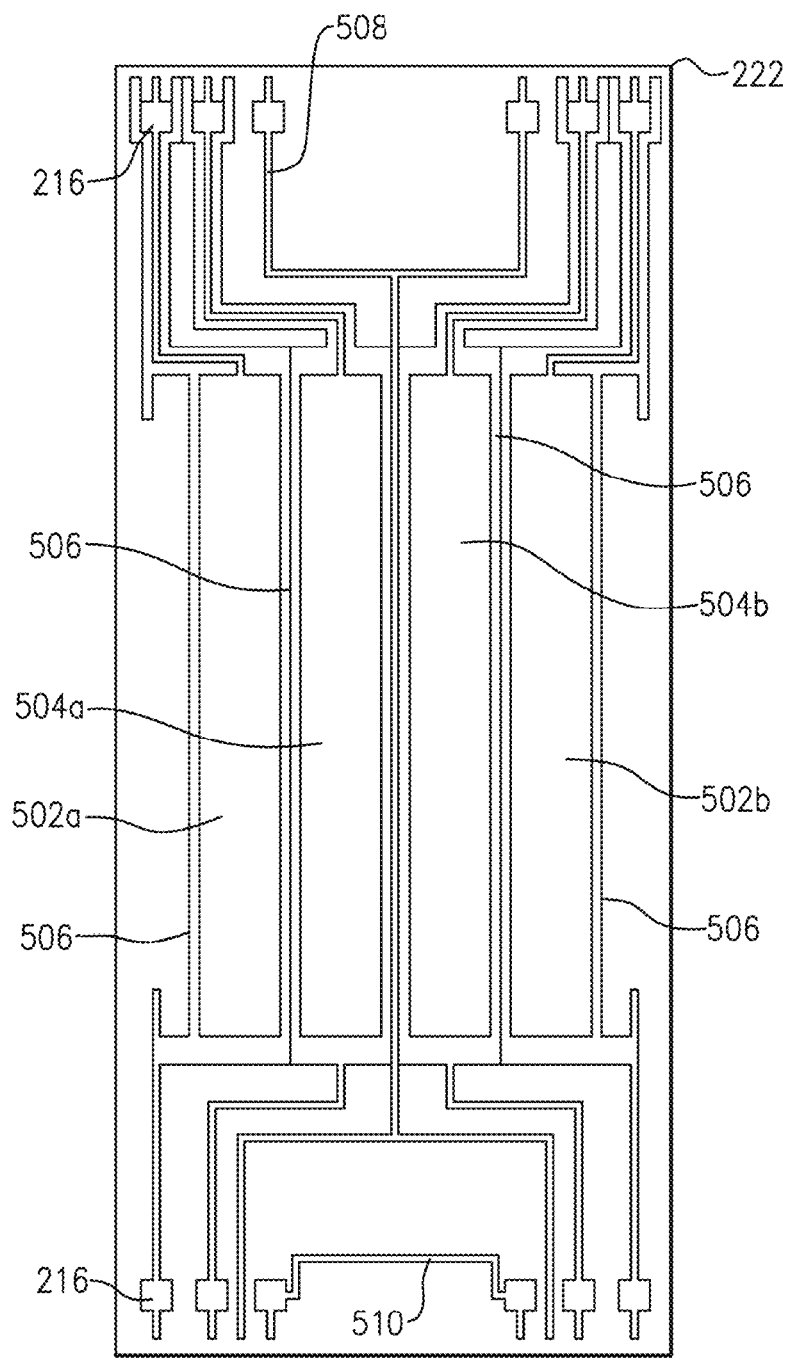
FIG. 5 is a plan view of examples of sense electrodes and drive electrodes of an example of the electric field detector illustrated in FIG. 2A, according to examples discussed herein.

Referring now to FIG. 5, illustrated is a plan view of one example of sense electrodes 502a, 502b (collectively "sense electrodes 502") and drive electrodes 504a, 504b (collectively "drive electrodes 504") of the electric field detector 200 (which, as discussed above, may be implemented in connection with the electric field detector 1100, the one or more electric field detectors 1202, and/or the one or more electric field detectors 1306) illustrated in FIGS. 2A and 2B. For simplicity, FIG. 5 illustrates the sense electrodes 502 and the drive electrodes 504 implemented in an example of the electric field detector 200 in which the electric field detector 200 detects aspects of an electric field in one dimension only, that is, in which the proof mass 202 only rotates about a single torque axis. In other examples, in which the electric field detector 200 is configured to detect aspects of an electric field in multiple orthogonal dimensions, the sense electrodes 502 and drive electrodes 504 may include additional electrodes, substantially similar to the electrodes 502, 504, oriented in an orthogonal dimension from the electrodes 502, 504. For example, whereas the sense electrodes 502a, 502b are positioned along an x-axis, an additional set of sense electrodes could be implemented and positioned along the y-axis to detect an orthogonal component of an electric field. The additional set of sense electrodes could be implemented in the same plane as the sense electrodes 502, or implemented in a different plane as the sense electrodes 502 (for example, in a different plane along the z-axis).

Returning to the example illustrated by FIG. 5, FIG. 5 illustrates the electrical connections between the sense electrodes 502 and the corresponding electrical contacts 216, and the electrical connections between the drive electrodes 504 and the corresponding electrical contacts 216. As previously discussed, leads 218 may couple electrical contacts 216 on the substrate 122 and electrical contacts 216 on the baseplate 214 to the control circuit. For the convenience of illustration, leads 218 are not shown in FIG. 5. As discussed above with reference to FIGS. 2A and 2B, in various examples the sense electrodes 502 and the drive electrodes 504 are formed on the substrate 222, and in particular, within the substrate offset space beneath the proof mass 202. FIG. 5 is described with continuing reference to the electric field detector 200 illustrated in FIGS. 2A and 2B, and the components thereof.

FIG. 5 illustrates a first sense electrode 502a (for example, a left sense electrode), a second sense electrode 502b (for example, a right sense electrode), a first drive electrode 504a (for example, a left torquer), and a second drive electrode 504b (for example, a right torquer). As further discussed with reference to FIGS. 7A-7C and FIGS. 8A-8C, each of the first sense electrode 502a, second sense electrode 502b, first drive electrode 504a, second drive electrode 504b, and electrical contacts 216 may be applied as a metallization layer to the substrate 222. For instance, each sense electrode 502, each drive electrode 502, and/or each electrical contact 216 may be a layer of chrome, platinum, or gold on the substrate 222. As previously described, one or both of the sense electrodes 502 may be used to measure a change in capacitance (for example, electrical capacitance) relative to the proof mass 202 as a result of torsional movement of the proof mass 202. One or both of the drive electrodes 504 may be used to produce a feedback torque on the proof mass 202 and reposition the proof mass 202.

In one example, the two sense electrodes 502a, 502b are used for a differential capacitance measurement, and the two drive electrodes 504a, 504b are used as torquers for force feedback during closed loop operation. Each sense electrode 502 and drive electrode 504 is interposed between a pair of respective electrical contacts 216 and extended along a length of the substrate 222. While shown in FIG. 5 as a pair of sense electrode plates and a pair of drive electrode plates, each plate having a substantially rectangular shape, in various other examples any suitable number of sense electrodes 502 and drive electrode 504 may be used (for example, by increasing a number of sense electrodes to detect aspects of an electric field in multiple dimensions), and each of the sense electrodes 502 or drive electrodes 504 may have any suitable shape. Moreover, in certain examples the first sense electrode 502a and the first drive electrode 504a may be connected and act as a single large electrode to maximize performance when not operating in a closed loop mode of operation. In such an example, the second sense electrode 502b and the second drive electrode 504b may be coupled in a similar manner. In certain examples, the sense electrodes 502 and the drive electrode 504 may be reversed and their relative areas chosen to optimize the relative level of performance between the drive and sense operations. In one example, the sense electrodes 502a, 502b (for example, the outer-positioned electrodes) act on the plurality of supports 206 of the detector 200, and therefore may have a greater effectiveness.

In various examples, each sense electrode 502 and drive electrode 504 may include a respective guard ring 506. As shown in FIG. 5, the proof mass 202 may also have a guard ring 508. Each guard ring 506 substantially surrounds the respective sense electrode or drive electrode and separates that sense electrode or drive electrode from the other sense electrode and drive electrode. In one example, each the guard ring 506 is a thin metal track that traces the perimeter of the corresponding plate or electrode. Each guard ring 506, 508 substantially eliminates direct-current (DC) current and low-frequency leakage currents from unintentionally affecting the corresponding sense electrodes 502, drive electrodes 504, or proof mass 202. DC current and low-frequency leakage current may limit the dynamic range of the electric field detector 200 and may create low-frequency noise by producing undesired voltages in the source impedances. FIG. 5 further shows a ground contact 510 for the proof mass 202.

Figure 6:
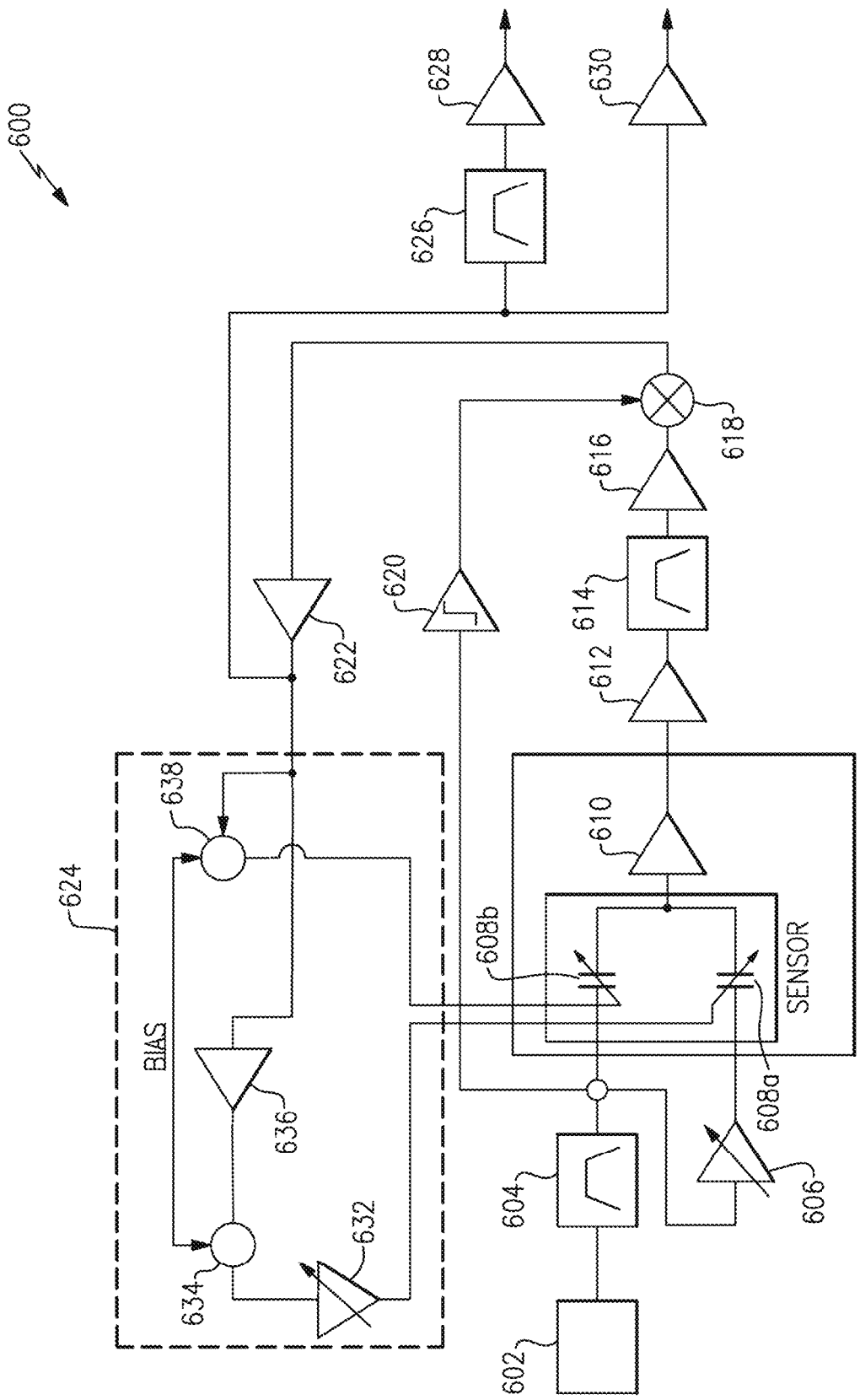
FIG. 6 is a block diagram of a control circuit according to examples discussed herein.

Turning now to FIG. 6, shown is one example of a control circuit 600 that may be coupled to the electric field detector 200 illustrated in FIGS. 2A and 2B, or that may be included in or be an example of the controllers discussed herein, including the controllers 1206, 1310, and 1322, to detect the characteristics of an electric field received at the detectors 200, 1100, 1202, 1306, and/or provide one or more control signals (for example, for driving the drive electrodes). For instance, the control circuit may be coupled to the contacts 216 illustrated in FIGS. 2A and 2B. FIG. 6 is discussed with continuing reference to the electric field detector 200 of FIGS. 2A and 2B, and the components thereof, for purposes of explanation.

In certain examples, the control circuit 600 may include any processor, multiprocessor, or controller. Furthermore, in some examples, the control circuit 600 may be coupled to an external controller, such as the controllers 1206, 1310, 1322. The processor may be connected to a memory and a data storage element. The memory stores a sequence of instructions coded to be executable by the processor to perform or instruct the various components discussed herein to perform the various processes and acts described herein. For instance, the control circuit 600 may communicate with, and provide one or more control signals to the sense electrodes and the drive electrodes of the electric filed detector via the contacts 216 and the leads 218. The memory may be a relatively high performance, volatile random-access memory such as a dynamic random-access memory or static random-access memory. However, the memory may include any device for storing data, such as a disk drive or other nonvolatile storage device.

The instructions stored on the data storage may include executable programs or other code that can be executed by the processor. The instructions may be persistently stored as encoded signals, and the instructions may cause the processor to perform the functions and processes described herein, such as providing one or more control signals to generate a feedback torque. The data storage may include information that is recorded, on or in, the medium, and this information may be processed by the processor during execution of instructions. The data storage includes a computer readable and writeable nonvolatile data storage medium configured to store non-transitory instructions and data. In addition, the data storage includes processor memory that stores data during operation of the processor.

In the illustrated example, the control circuit 600 includes a precision square-wave generator 602 which is coupled to a first filter 604. The precision square-wave generator 602 generates a signal which is converted to a sine wave by the first filter 604. The first filter 604 may include any suitable filter designed to accept a square-wave input and provide a sinusoidal output. For instance, one example is a low-Q active bandpass filter with a notch filter to reduce the third-order harmonic. In various examples, the first filter 604 has a very low amplitude sensitivity to temperature, such as 1-3 ppm per degree Celsius. The first filter 604 is coupled to an inverting amplifier 606 which has an adjustable gain and a nominal gain of −1. Accordingly, an output of the first filter 604 and the inverting amplifier 606 form a low-noise differential sine-wave carrier generator.

As shown in FIG. 6, the carrier generator may be coupled to each of the sense electrodes (for example, shown as readout capacitors 608a, 608b, collectively "readout capacitors 608") to excite the readout capacitors 608 in order to up-convert (for example, increase a frequency) an electronics signal produced by the received electric field. In various examples, by up-converting the received electric field information, the information is converted to a frequency where amplifier noise is significantly lower. Moreover, the up-conversion reduces the sensitivity of the electric field to current noise sources in a preamplifier 610 coupled to the readout capacitors 608. While not illustrated in FIG. 6, in many instances the control circuit 600 may include one or more passive high-pass filters interposed between the outputs of the carrier generator and the readout capacitors 608 to reduce low-frequency voltage noise coupled to the readout capacitors 608 from the carrier generator. Such an arrangement offers the benefit of reduced low-frequency torque noise.

Referring to the electric field detector 200 of FIG. 2A, in the absence of an electric field, there will be no torque on the proof mass 202 (in an ideal case). In such a situation, no electric field information is passed from the readout capacitors 608 (sense electrodes 502 in FIG. 5) to the preamplifier 610. However, when an electric field is present, the readout capacitors 608 provide a measured signal to the preamplifier 610, which in turn provides an output of a carrier signal amplitude-modulated by the electric field (for example, a double-sideband suppressed carrier signal).

In various examples, the control circuit 600 includes a second amplifier 612 and a second filter 614 coupled to the output of the preamplifier 610. For instance, the second amplifier 612 may include a low-noise instrumentation amplifier with an input-referred noise density that is substantially less than the output-referred noise density. For example, the second amplifier 612 may include, or be coupled to, a chopping amplifier configured to reduce instrumentation noise. The carrier signal amplitude-modulated by the electric field is received and amplified by the second amplifier 612 before being filtered by the second filter 614 and received at a demodulator 618. According to certain examples, the second filter 614 includes a band-pass filter which has a low quality factor to reduce the noise within the amplitude-modulated carrier signal at the third order and higher order harmonics. Accordingly, the second filter 614 provides filtering functionality to prevent higher order harmonics from affecting the noise performance of the control circuit 600 after the carrier signal has been demodulated. In certain implementations, the control circuit 600 may also include a third amplifier 616 which is coupled to an output of the second filter 614 and configured to add an additional gain to the carrier signal amplitude-modulated by the electric field information. While illustrated in FIG. 6 as separated from the second filter 614, in certain examples the third amplifier 616 provides additional AC gain and may be incorporated into the second filter 614.

As shown in FIG. 6, the control circuit 600 includes a demodulator 618 and comparator 620 which are coupled to form a switching (or square wave) demodulator. In FIG. 6, the switching demodulator is coupled to an output of the third amplifier 616. The demodulator 618 drives a controller 622, which is coupled to the output of the demodulator 618. In some examples, the controller 622 may include an Integral-Derivative (ID) controller, a Proportional-Integral-Derivative (PID) controller, or any other suitable predictive controller. In one example, the controller 622 drives a torque generator 624 which produces a bias voltage at each respective torque generator electrode (for example, drive electrodes 504a, 504b illustrated in FIG. 5). In particular, the torque generator may produce respective torque generator voltages of (BIAS+K*−$V_C$) and (BIAS−K*$V_C$), where "BIAS" is a bias voltage, "K" is a scaling constant, and "$V_C$" is the output of the controller 622. For example, the torque generator 624 may produce a substantially constant bias voltage having a nominal value near one-half of the positive or negative supply voltage. While in the illustrated example, the torque generator 624 includes summation blocks 634, 638, an inverting gain 636, and an adjustable gain 632 for the purpose of illustration, in various other examples the torque generator 624 may be implemented with various other suitable components.

Accordingly, the applied torque, which is proportional to the square of the voltage, is directly proportional to the output of the controller 622. Such a biasing arrangement achieves a linearization of the closed-loop feedback torque applied to the proof mass 202 with respect to the output of the controller 622. This arrangement results in a linear control loop and permits a linear readout of the electric field information. In certain examples, the control circuit 600 may further include one or more passive low-pass filters (not shown) interposed between the torque generator 624 and the torque generator electrodes in order to reduce carrier-band noise applied to the torque generator electrodes.

As further illustrated in FIG. 6, the control circuit 600 may include a baseband filter 626 coupled to the output of the controller 622. For example, the baseband filter 626 may include a bandpass filter having a passband selected to extract the electric field information within the desired bandwidth from the output of the demodulator 618. The output of the baseband filter 626 may then be amplified by a fourth amplifier 628 and provided to an output of the control circuit 600 or one or more downstream diagnostic electronics. In at least one example, the fourth amplifier 628 is designed such that most of a variable voltage range of the amplifier 628 corresponds to a maximum expected in-band field strength of the electric field. Such a design provides the benefit of reduced noise. For instance, the fourth amplifier 628 may include a high-gain amplifier that has a gain of about 100. The parameters of the fourth amplifier 628 may be selected in conjunction with the parameters of the baseband filter 626 to select and amplify a desired frequency band (for example, a frequency band associated with brain activity (0.5 Hz-100 Hz)). As shown, in certain examples the control circuit 600 may also include a fifth amplifier 630 to provide an unfiltered output for diagnostic purposes.

Though the features within FIG. 6 are illustrated as blocks within a block diagram, unless otherwise indicated, the features may be implemented as signal processing circuitry, and may be implemented with one or more specialized hardware components or one or more specialized software components. For instance, the control circuit 600 may be implemented as one of, or a combination of, analog circuitry or digital circuitry. The control circuit 600 may be composed of an array of logic blocks arranged to perform one or more of the corresponding signal processing operations described herein. In particular, the processing circuitry may be implemented by an array of transistors arranged in an integrated circuit that provides a performance and power consumption similar to an ASIC (application-specific integrated circuit) or an FPGA (field-programmable gate array). In other examples, components of the control circuit 600 may be implemented as one or more microprocessors executing software instructions (for example, predefined routines). In particular, the software instructions may include digital signal processing (DSP) instructions. Unless otherwise indicated, signal lines may be implemented as discrete analog or digital signal lines, or as a single discrete digital signal line with appropriate signal processing to process separate signals.

Turning now to FIGS. 7A-7C and FIGS. 8A-C, illustrated is an example of a process 700 for fabricating an electric field detector, such as an example of the electric field detector 200 illustrated in FIGS. 2A-2B and FIG. 3. More particularly, FIGS. 7A-7C and 8A-8C illustrate a process 700 for fabricating an example of the electric field detector 200 being configured to detect aspects of an electric field in one dimension. An alternate process may apply to fabricating an example of the electric field detector 200 being configured to detect aspects of an electric field in multiple dimensions, such as by including additional acts involving the fabrication of sense electrodes.

Figure 7A:
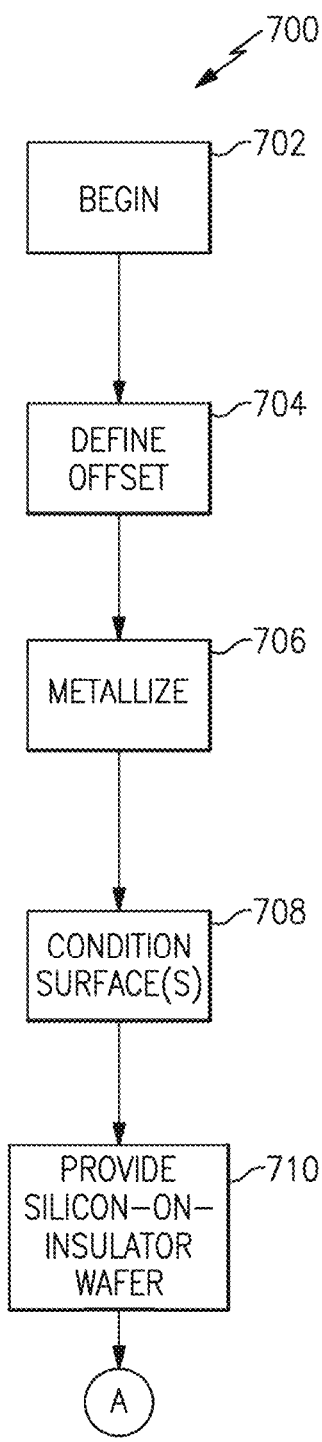
FIG. 7A-7C is a process flow for fabricating an example of an electric field detector, according to examples discussed herein.
Figure 8A:
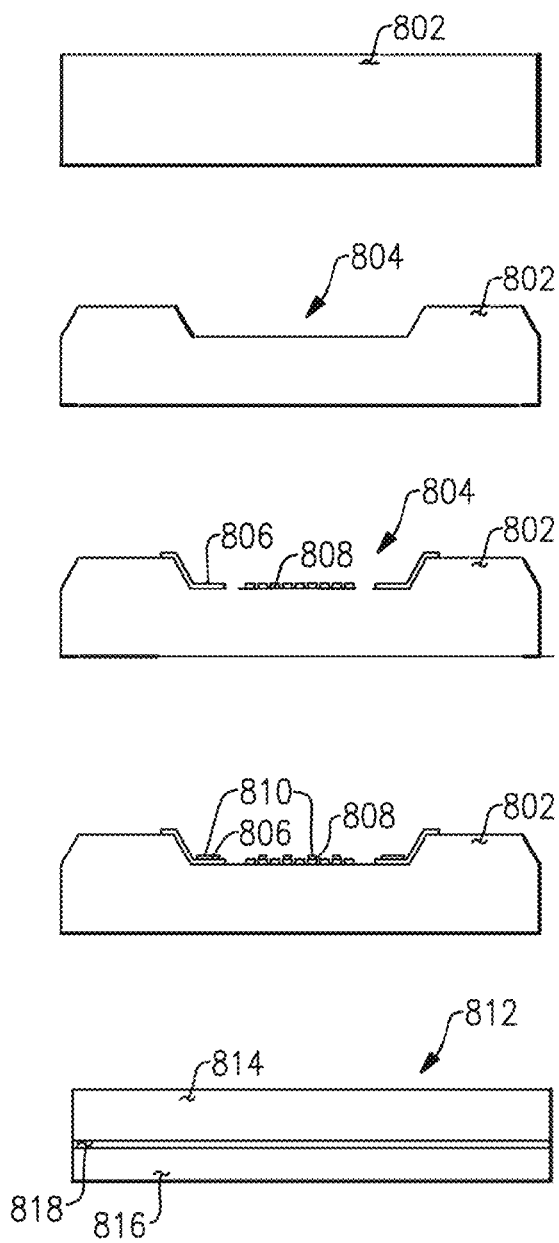
FIGS. 8A-8C show a state of an electric field detector during each act of the process flow of FIG. 7A-7C, according to examples discussed herein.
Figure 7B:
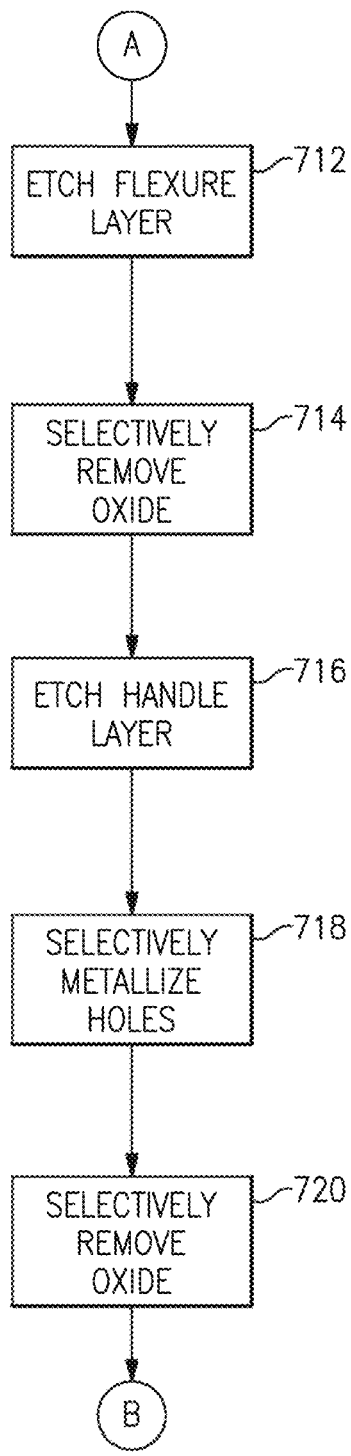
Figure 8B:
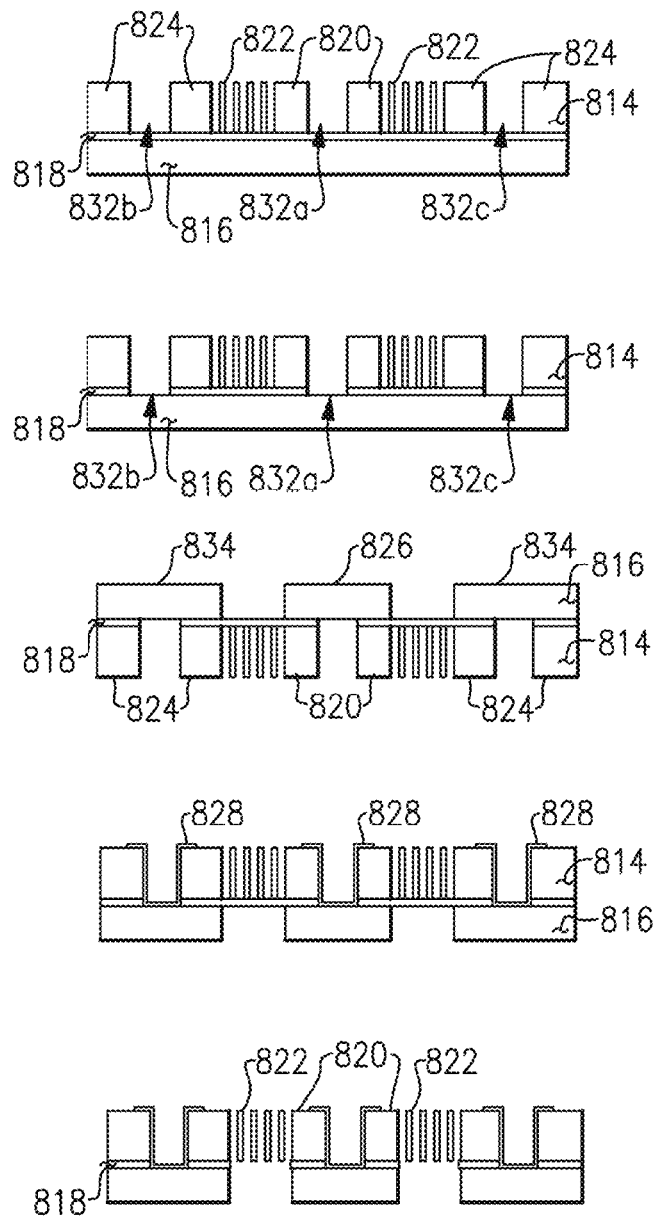
Figure 7C:
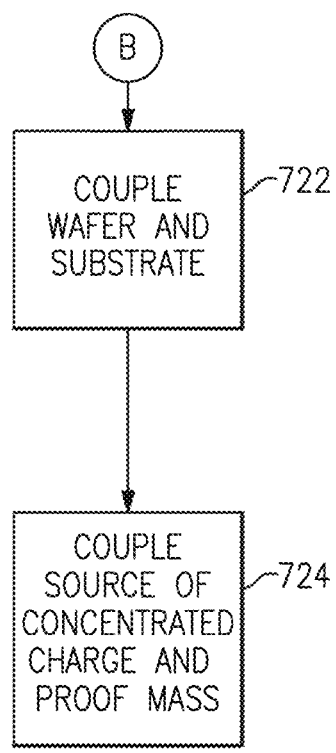
Figure 8C:
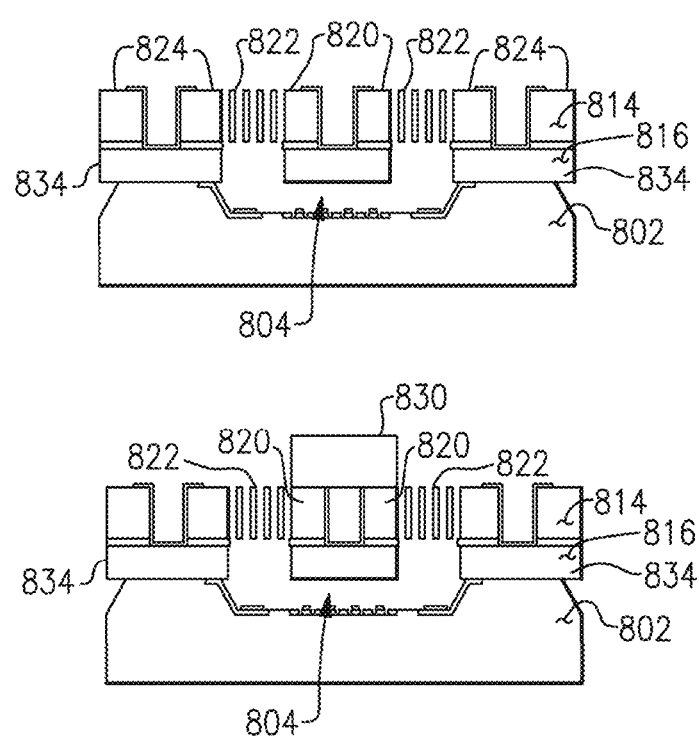

FIGS. 7A-7C illustrates the process flow and FIGS. 8A-8C show a state of an electric field detector during each act of the process 700. Each act of the process 700 of FIG. 7A-7C is illustrated immediately adjacent the corresponding state of production of the electric field detector. Accordingly, in some examples, the electric field detector shown in FIGS. 8A-8C may be one implementation of the electric field detector 200 described with reference to at least FIGS. 2A and 2B. That is, at least the source of concentrated charge, the substrate, the support(s), the proof mass, the sense electrode(s), and the drive electrode(s) described with reference to FIGS. 8A-8C may correspond to examples of the source of concentrated charge, the support(s), the proof mass, the sense electrode(s), and the drive electrode(s) previously described with reference to at least FIGS. 2A and 2B, as well as, the sense electrode(s) and the drive electrode(s) described with reference to FIG. 5.

The process 700 begins at act 702 which may include the act of providing a substrate wafer 802 (referred to generally as the "substrate 802"). In various examples, the substrate 802 is a glass wafer. The glass wafer may be doped such that it conducts electricity at elevated temperatures (for example, about 350 degrees Celsius). The glass wafer may be composed of borosilicate, for example. In act 704, the process 700 includes defining a well 804 (for example, a substrate offset space) in the substrate 802. In certain examples, the substrate offset space is formed by etching the substrate 802; however, other processing techniques may be used, such as milling, grinding, or one or more deposition processes. For instance, the etching process may be implemented using the MESA™ etch system offered by APPLIED MATERIALS™ of Santa Clara, California Areas of the substrate 802 which are not etched during act 704 may be later coupled to a flexure layer 814 or a handle layer 816 of a structure wafer 812, as discussed below.

In act 706, the process 700 may include depositing a conducting material, such as metal, on the substrate 802 to form one or more sense electrodes 806, one or more drive electrodes 808, and/or one or more guard rings and electrical contacts (not shown). In the shown example, the conducting material is primarily deposited within the substrate offset space 804. For instance, each sense electrode 806 and each drive electrode 808 may be formed on a surface of the substrate 802 within the substrate offset space 804. As discussed with reference to FIGS. 2A and 2B, each sense electrode 806 may be configured to measure a change in capacitance within the substrate offset space 804 (for example, between the sense electrode and a proof mass), and each drive electrode 808 may be configured to act as a closed loop torquer on the proof mass. Each guard ring is formed on the substrate 802 to substantially surround a corresponding one of the sense electrodes 806 or drive electrodes 808 and isolate that respective sense or drive electrode plate 806, 808 from the effects of DC current and low-frequency leakage currents. In other examples of a fabrication process, depositing a conducting material to form one or more sense electrodes may include forming an a different number of sense electrodes (for example, additional sense electrodes) where an electric field detector being fabricated is configured to detect aspects of an electric field in multiple dimensions.

In act 708, the process 700 may include conditioning the surface(s) of one or more sense electrodes 806 and/or drive electrodes 808 to increase the surface texture thereof. In one example, act 708 may include applying one or more small metal bumps 810 to the surface of the sense electrodes 806 and/or drive electrodes 808. The increase in surface texture decreases the holding force between the substrate 802 and the structure wafer 812 by reducing the contact area between the substrate 802 and the structure wafer 812.

In act 710, the process 700 may include providing a structure wafer 812, such as an SOI wafer. While an SOI wafer is used as one example for the purpose of explanation, in various other examples other suitable structure wafer materials may be used, such as quartz, polysilicon, etc. In the shown example of FIGS. 8A-8C, the structure wafer 812 includes a flexure layer 814 and a handle layer 816 separated by a buried oxide layer 818. In one example, the flexure layer 814 is about 400 μm thick (for example, ±2 μm thickness), the handle layer 816 is about 300 μm thick (for example, ±2 μm thickness), and the buried oxide 818 is about 2 μm thick (for example, ±1 μm thickness).

Referring to FIG. 7B and FIG. 8B, in act 712 the process 700 may include defining a proof mass 820, a plurality of supports 822, and/or one or more anchors 824 in the structure wafer 812. In the shown example of FIG. 8B, each support 822 is interposed between the proof mass 820 and a respective anchor 824. In certain examples, the proof mass 820, the plurality of supports 822, and/or one or more anchors 824 are formed by etching the flexure layer 814 of the structure wafer 812; however, other processing techniques may be used, such as milling, grinding, or one or more deposition processes. In certain examples, a Deep Reactive Ion Etch (DRIE) process may be used with a dry etch tool and Inductively Coupled Plasma (ICP) to define each of the proof mass 820, supports 822, and the anchors 824. In one example, the ICP etch may also define one or more holes in the flexure layer 814. Each hole may be used to electrically connect the flexure layer 814 and the handle layer 816, as described during later processing acts of FIG. 7A-7C. In FIG. 7B, the flexure layer 814 is shown as having a hole 832a within the proof mass 820 and a hole 832b, 832c within each anchor 824.

In act 714, the process 700 may include selectively removing a first portion of the oxide layer 818 from the structure wafer 812. In particular, the first portion may include those areas of the oxide layer 818 that were exposed during the etching process of act 712. That is, in one example act 714 may include removing the exposed oxide from the holes 832a, 832b, 832c in the flexure layer 814. For instance, an oxide ICP etch may be used to remove the exposed oxide. Following act 714, in act 716 the process 700 may include defining one or more counterbalances in the handle layer 816 of the structure wafer 812. For instance, act 716 may include etching the handle layer 816 to define a counterbalance 826 for the proof mass 820. In act 716, the process 700 may further include defining one or more anchor grounds 834. Each anchor ground 834 couples a respective anchor 824 to the substrate 802, as further discussed below with reference to act 722.

In act 718, the process 700 may include selectively metallizing each recess formed in the flexure layer 814 of the structure wafer 812 to plate the one or more formed recesses. The deposited metal 828 forms an electrical connection between the flexure layer 814 and the handle layer 816. Following act 718, in act 720 the process 700 includes the act of etching a second portion of the oxide layer 818. As shown in FIG. 8B, the second portion of the oxide layer 818 may include those sections of the oxide layer 818 that are attached to the supports 822. Accordingly, act 720 may include releasing the supports 822 from the oxide layer 818 to suspend the proof mass 820. In at least one example, the supports 822 are released by removing the second portion of the oxide layer 818 using a hydrofluoric acid etching process.

Once each of the supports 822 has been released, the process 700 may include coupling the structure wafer 812 to the substrate 802, as shown in FIG. 8C. In one example, the handle wafer 816 may be anodically bonded to the substrate 802. Once the structure wafer 812 has been coupled to the substrate 802, the proof mass 820 may be suspended above and partially within the substrate offset space 804 by the plurality of supports 822. The anchor grounds 834 may couple the flexure layer 814 to the substrate 802 at each end of the flexure layer 814 (for example, at each anchor 824), where the substrate offset space 804 is substantially in the center of the substrate 802. In an example where multiple electric field detectors are fabricated from the same of substrate 802 material and structure wafer 812 (for example, SOI wafer), the process 700 may then include dicing each sheet to separate each of the separate electric field detectors. The process 700 ends in act 724, in which a source of concentrated charge 830 is coupled to the structure wafer 812, and in particular, coupled to the proof mass 820. As shown, the source of concentrated charge 830 is positioned at about the center of the flexure layer 814 such that each of the supports 822 suspends the source of concentrated charge 830 above the substrate offset space 804. As discussed above, the source of concentrated charge 830 may be polarized before or after it has been coupled to the flexure layer 814. Processes and acts for operating the electric field detector once it has been fabricated are discussed above with reference to the electric field detector 200 shown in FIGS. 2A, 2B, and 3.

As discussed above, in various examples the assembled electric field detector may be packed with a housing, a baseplate, and one or more electrical connections, such as the housing 210 and the baseplate 214 illustrated in FIGS. 2A and 2B and the electrical connections illustrated in FIG. 5. In various examples, the source of concentrated charge 830 may be coupled to the flexure layer 814 early in the packaging process (for example, before the sense electrodes 806 and/or drive electrodes 808 are electrically bonded to the substrate 802). However, in other examples, the source of concentrated charge 830 may be coupled to the flexure layer 814 as part of a vacuum sealing process with the housing, after integration in a sensor array, or during operation. In one particular example, an uncharged electret is attached to the flexure layer 814 and subsequently charged as part of a vacuum sealing process. For instance, once the detector is placed in the vacuum, an electron beam source may embed a charge on one or more surfaces of the uncharged electret to generate an electric dipole. The housing may then be attached to the baseplate of the detector to form a hermetic seal. Such a process provides the benefit of reducing air damping during operation of the detector. In other examples, charge can also be added after the housing is attached to form a hermetic seal, or continuously during operation, as is the case of an active system, where a voltage excitation is used to form an AC electric dipole on the proof mass, examples of which are discussed above with respect to FIGS. 11A and 11B.

As discussed above, certain electric field detectors, including the electric field detector 200, may detect an electric field in a one or more dimensions (for example, one or two dimensions of three-dimensional space). In some examples, it may be beneficial to detect aspects of an electric field in multiple dimensions (for example, in two or three dimensions of three-dimensional space). Detecting aspects of an electric field in multiple dimensions may be achieved by implementing multiple electrical field detectors configured to detect an electric field in one direction (also referred to as a one-axis electric field detector) and oriented orthogonally from one another. For example, a sensing system may include three or more one-axis electric field detectors, similar to implementations of the electric field detector 200 being configured to detect aspects of an electric field in one dimension, each oriented orthogonally from one another, such that an electric field is detected in all three dimensions.

In other examples, electric field detectors may be configured to detect aspects of an electric field in multiple dimensions. For example, an electric field detector may detect an electric field in two dimensions (also referred to as a two-axis electric field detector), such as certain implementations of the electric field detector 200. In another example, an electric field detector may detect an electric field in three dimensions (also referred to as a three-axis electric field detector). To detect an electric field in all three dimensions of three-dimensional space, a sensing system may include a two-axis electric field detector and a one-axis electric field detector, two two-axis electric field detectors, a single three-axis electric field detector, or any other combination of electric field detectors. Additional example of two-axis electric field detectors, and examples of three-axis electric field detectors, are provided below.

Figure 14:
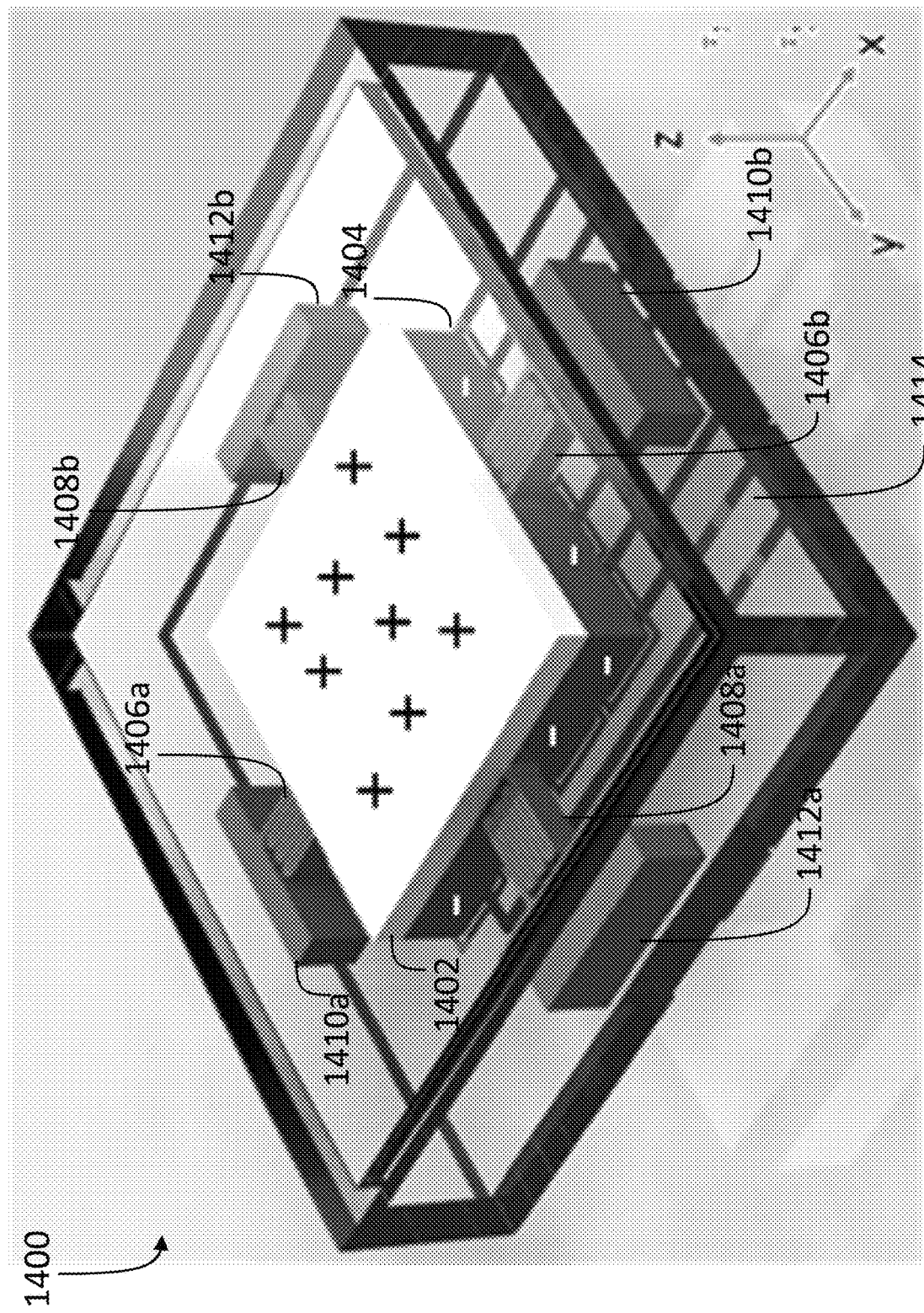
FIG. 14 illustrates a perspective view of an electric field detector according to an example.

FIG. 14 illustrates a perspective view of an electric field detector 1400 according to an example. The electric field detector 1400 includes a source of concentrated charge 1402, a proof mass 1404, a first set of supports 1406 including a first support 1406a and a second support 1406b, a second set of supports 1408 including a third support 1408a and a fourth support 1408b, a first set of anchors 1410 including a first anchor 1410a and a second anchor 1410b, a second set of anchors 1412 including a third anchor 1412a and a fourth anchor 1412b, and a baseplate 1414.

The electric field detector 1400 is substantially similar to the electric field detector 200. However, rather than having one set of supports 206, the electric field detector 1400 includes two sets of supports 1406, 1408. The proof mass 1404 may be configured to rotate about two axes, depending on a polarization of the source of concentrated charge 1402, and may be configured to detect aspects of an electric field in at least two dimensions (for example, the two dimensions of three-dimensional space along which the source of concentrated charge 1402 is not polarized). The additional supports provide a more symmetrical design of the electric field detector 1400, which facilitates rotation of the electric field detector 1400 in multiple dimensions. For example, the additional supports may suppress movement and/or rotation of the electric field detector 1400 that is not caused predominantly by an external electric field that the electric field detector 1400 is intended to detect.

For example, where the source of concentrated charge 1402 is polarized along the z-axis, as illustrated in the example of FIG. 14, the electric field detector 1400 may be configured to detect aspects of an electric field in the x-axis (for example, based on rotation of the proof mass 1404 about the y-axis) and aspects of the electric field in the y-axis (for example, based on rotation of the proof mass 1404 about the x-axis). In another example, where the source of concentrated charge 1402 is polarized along the x-axis, the electric field detector 1400 may be configured to detect aspects of an electric field in the y-axis (for example, based on rotation of the proof mass 1404 about the z-axis) and aspects of the electric field in the z-axis (for example, based on rotation of the proof mass 1404 about the y-axis). In another example, where the source of concentrated charge 1402 is polarized along the y-axis, the electric field detector 1400 may be configured to detect aspects of an electric field in the x-axis (for example, based on rotation of the proof mass 1404 about the z-axis) and aspects of the electric field in the z-axis (for example, based on rotation of the proof mass 1404 about the x-axis). Similar to the electric field detector 200, torsional movement of the proof mass 1404 may be detected based on variations in capacitance between the proof mass 1404 and one or more sense electrodes.

Accordingly, the electric field detector 1400 may be particularly well-suited to determine aspects of an electric field in multiple (for example, two) dimensions. A polarization of the source of concentrated charge 1402 may be selected to determine which aspects of the electric field that the electric field detector 1400 determines. In some examples, multiple implementations of the electric field detector 1400 may be implemented together. For example, a first example of the electric field detector 1400 may be implemented in which the source of concentrated charge 1402 is polarized along a first axis, and a second example of the electric field detector 1400 may be implemented in which the source of concentrated charge 1402 is polarized along a second axis, orthogonal to the first axis. If both of these two example detectors are implemented together, then all three orthogonal axes of an electric field may be detected, with one dimension being redundantly determined by both detectors (more particularly, a dimension of the electric field along the axis that is orthogonal to both the first axis and the second axis).

As discussed above with respect to FIGS. 11A and 11B, in some examples, a source of concentrated charge may be replaced by a dielectric material coupled to one or more electrodes to form a dynamic electric dipole. For example, with reference to the electric field detector 1400, the source of concentrated charge 1402 may be replaced by a dielectric material coupled to one or more electrodes to form a dynamic electric dipole, as discussed with respect to FIG. 15.

Figure 15:
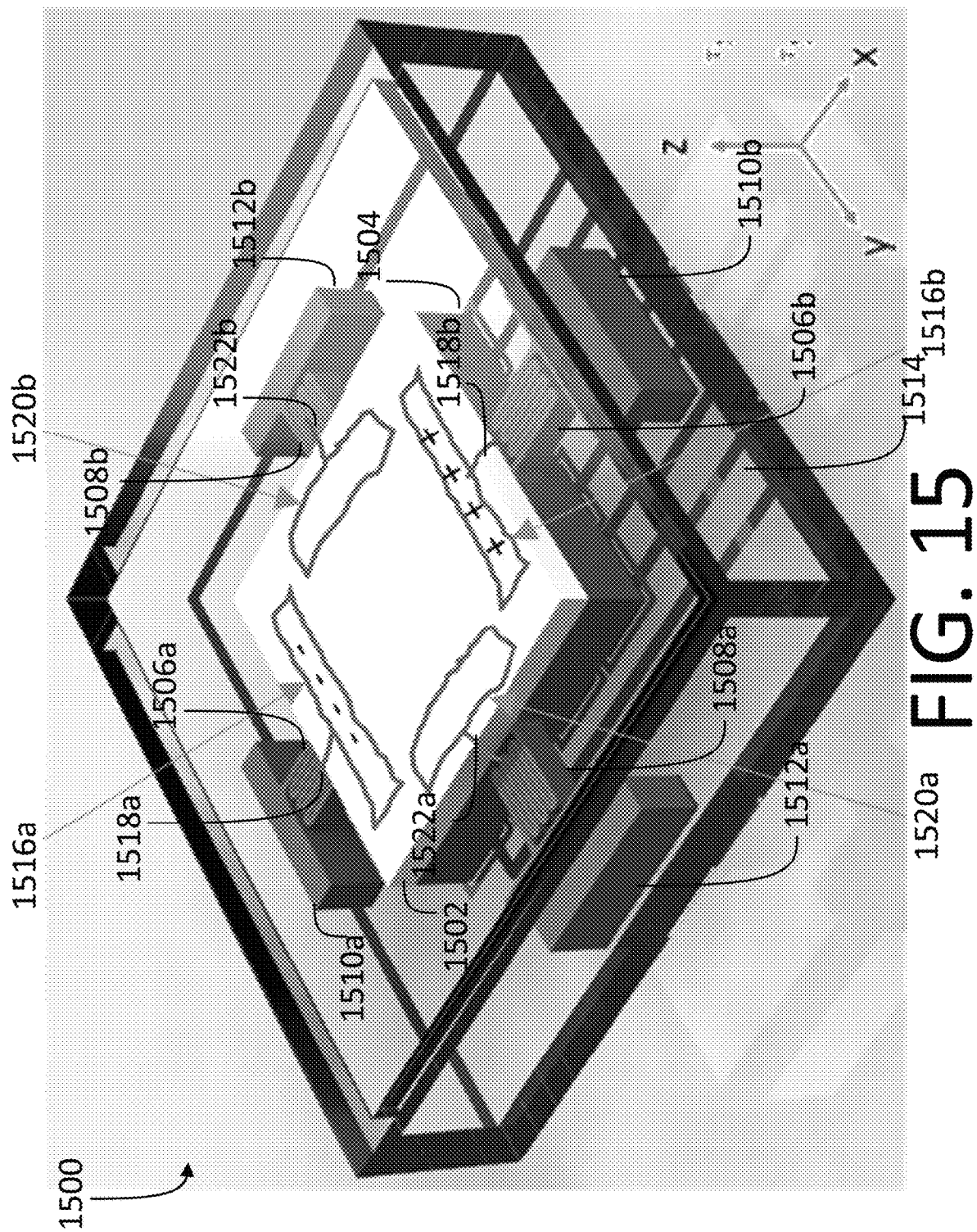
FIG. 15 illustrates a perspective view of an electric field detector according to an example.

FIG. 15 illustrates a perspective view of a monolithic electric field detector 1500 according to an example. The electric field detector 1500 includes a dielectric material 1502, a proof mass 1504, a first set of supports 1506 including a first support 1506a and a second support 1506b, a second set of supports 1508 including a third support 1508a and a fourth support 1508b, a first set of anchors 1510 including a first anchor 1510a and a second anchor 1510b, a second set of anchors 1512 including a third anchor 1512a and a fourth anchor 1512b, a baseplate 1514, a first set of electrodes 1516 (also referred to herein as a first set of "polarization electrodes") including a first electrode 1516a and a second electrode 1516b, a first set of traces 1518 including a first trace 1518a and a second trace 1518b, a second set of electrodes 1520 (also referred to herein as a second set of polarization electrodes) including a third electrode 1520a and a fourth electrode 1520b, and a second set of traces 1522 including a third trace 1522a and a fourth trace 1522b.

The electric field detector 1500 may include one or more power sources (not illustrated) and/or one or more control circuits (not illustrated). The power source(s) may be coupled to each of the traces 1518, 1522 to apply a respective voltage to each of the electrodes 1516, 1520. For example, the control circuit(s) may control the power source(s) to apply a positive voltage (relative to a reference voltage, such as ground) to one of the electrodes 1516a, 1516b, and a negative voltage (relative to the reference voltage) to the other of the electrodes 1516a, 1516b to generate a potential difference between the electrodes 1516a, 1516b and thereby polarize the dielectric material 1502 along the x-axis (also referred to herein as a "first polarization axis"). Similarly, the control circuit(s) may control the power source(s) to apply a positive voltage (relative to a reference voltage, such as ground) to one of the electrodes 1520a, 1520b, and a negative voltage (relative to the reference voltage) to the other of the electrodes 1520a, 1520b to generate a potential difference between the electrodes 1520a, 1520b and thereby polarize the dielectric material 1502 along the y-axis (also referred to herein as a "second polarization axis").

Accordingly, the control circuit(s) may control the power source(s) to polarize the dielectric material 1502 along either or both of the x-axis and the y-axis. When the dielectric material 1502 is polarized along the x-axis by the electrodes 1516, a y-component and a z-component of an electric field may be determined based on rotation of the proof mass 1504 about the z-axis and the y-axis, respectively. Similarly, when the dielectric material 1502 is polarized along the y-axis by the electrodes 1520, an x-component and a z-component of the electric field may be determined based on rotation of the proof mass 1504 about the z-axis and the x-axis, respectively. Thus, by selectively polarizing the dielectric material 1502 in multiple axes, the monolithic electric field detector 1500 is capable of determining aspects of an electric field in all three dimensions of three-dimensional space.

More particularly, a polarization of the dielectric material 1502 by the electrodes 1516 along the x-axis may be expressed as, $$p_x = (V_a - V_b) * \sin(f_1 * t)$$

where $p_x$ is a polarization of the dielectric material 1502 along the x-axis, $V_a$ is a voltage of the first electrode 1516a, $V_b$ is a voltage of the second electrode 1516b, $f_1$ is a frequency of a voltage provided to the electrodes 1516 by the power source(s), and t is time. Based on this, aspects of an electric field may be determined as, $$E_y = \frac{\tau_z}{p_x}$$

and $$E_z = \frac{\tau_y}{p_x}$$

where $E_y$ is a y-component of the electric field, $\tau_z$ is a torque of the proof mass 1504 about the z-axis, $E_z$ is a z-component of the electric field, and $\tau_y$ is a torque of the proof mass 1504 about the y-axis, the torques being determined based on measurements from sensors, such as capacitance sensors, as discussed above. For example, the baseplate 1514 may be coupled to one or more sets of one or more capacitors (not illustrated) configured to sense a change in capacitance resulting from torque of the proof mass 1504. Accordingly, a y- and z-component of an electric field may be determined based on the polarization of the dielectric material 1502 along the x-axis by the power source(s) and/or control circuit(s).

Similarly, a polarization of the dielectric material 1502 by the electrodes 1520 along the y-axis may be expressed as, $$p_y = (V_c - V_d) * \sin(f_2 * t)$$

where $p_y$ is a polarization of the dielectric material 1502 along the y-axis, $V_c$ is a voltage of the third electrode 1520a, $V_d$ is a voltage of the fourth electrode 1520b, $f_2$ is a frequency of a voltage provided to the electrodes 1520 by the power source(s), and t is time. Based on this, aspects of an electric field may be determined as, $$E_x = \frac{\tau_z}{p_y}$$

and $$E_z = \frac{\tau_x}{p_y}$$

where $E_x$ is an x-component of the electric field, $\tau_z$ is a torque of the proof mass 1504 about the z-axis, $E_z$ is a z-component of the electric field, and $\tau_x$ is a torque of the proof mass 1504 about the x-axis, the torques being determined based on measurements from sensors, such as capacitance sensors, as discussed above. For example, the baseplate 1514 may be coupled to one or more sets of one or more capacitors (not illustrated) configured to sense a change in capacitance resulting from torque of the proof mass 1504. Accordingly, an x- and z-component of an electric field may be determined based the polarization of the dielectric material 1502 along the y-axis by the power source(s) and/or control circuit(s).

Thus, the electric field detector 1500 may be configured to detect aspects of an electric field in all three dimensions of three-dimensional space. In the example provided above, the electric field detector 1500 detects an x-, y-, and z-component of an electric field, including redundantly detecting the z-component of the electric field based on both polarizations of the dielectric material 1502. In other examples, the electric field detector 1500 may include additional electrodes to polarize the dielectric material 1502 along the z-axis as well, in addition to or in lieu of the electrodes 1516, 1520. That is, in some examples, the electric field detector 1500 may include any combination of electrodes to polarize the dielectric material 1502 in any number and combination of dimensions, such that the electric field detector 1500 may detect aspects of an electric field in any number and combination of dimensions.

As discussed above, the electrodes 1516, 1520 may be driven by power source(s) and/or controller(s) at respective AC frequencies $f_1$, $f_2$. For example, the AC frequencies $f_1$, $f_2$ may range from approximately 20 kHz to approximately 1 MHz in some examples. In some examples, the frequencies $f_1$, $f_2$ are different from one another such that the electrodes 1516, 1520 may be simultaneously polarize the dielectric material 1502 in two dimensions, with the electric field components $E_y$, $E_z$ being up-converted to frequency $f_1$ and the electric field components $E_x$, $E_z$ being up-converted to frequency $f_2$. In this manner, the electric field components $E_y$, $E_z$ may be differentiated from the electric field components $E_x$, $E_z$ because they correspond to (for example, are up-converted to) the different frequencies $f_1$, $f_2$. The electric field components may subsequently be separately identified by de-modulating the electric field components to identify a baseband signal. A frequency of the baseband signal (that is, one of frequencies $f_1$, $f_2$) is recovered to associate the correct electric field components with the recovered baseband signal frequency. Thus, the frequencies $f_1$, $f_2$ may be differentiated to uniquely identify one or more dimensions associated with the electric field components.

As such, in addition to providing improved electric field detectors that exploit the electric component of electromagnetic signals, various other aspects and examples discussed herein provide improved fabrication processes for efficiently and cost-effectively producing a compact electric field detector. Particular examples of the electric field detector may include an electric field detector capable of detecting bio-physical signals generated by the body of a patient or user, such as the electric field of his or her brain, heart, nerves or muscles. When compared to available electromagnetic sensors examples of the electric field detector herein achieve a low noise (for example, less than 1 mV/m/rtHz at 10 Hz) at a compact size (for example, less than 1 cm$^3$) and a low production cost.

As discussed above, in some embodiments, movement of a proof mass (for example, any of the proof masses 202, 1102, 1404, 1504) may be determined based on one or more capacitive sensors. In other examples, other sensors may be implemented to determine movement of a proof mass in addition to or in lieu of the capacitance sensors. For example, an optical sensor may be implemented to optically determine movement of the proof mass, and determine parameters of an electric field therefrom. In another example, a resistive sensor may be implemented having a resistance that varies based on movement of the proof mass. Variations in the resistance of the resistive sensor may be determined (for example, by identifying variations in a signal provided to the resistive sensor and determining variations in the resistance of the resistive sensor therefrom), and parameters of an electric field generating the variations in the resistance of the resistive sensor may be determined therefrom.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the disclosure. Accordingly, the foregoing description and drawings are by way of example only, and the scope of the disclosure should be determined from proper construction of the appended claims, and their equivalents.

What is claimed is:

1. A sensor system comprising:
   a first substrate configured to be coupled to a user;
   an electric field detector to detect an electric field generated by the user, the electric field detector being coupled to the first substrate and comprising:
   a second substrate;
   a proof mass positioned above the second substrate;
   one or more electrodes coupled to the second substrate; and
   a control circuit coupled to the one or more electrodes, the control circuit being configured to determine a respective change in capacitance between the proof mass and each respective electrode of the one or more electrodes responsive to torsional movement of the proof mass in response to the electric field; and
   a controller coupled to the first substrate and to the electric field detector, the controller being configured to:
   receive, from the electric field detector, information indicative of each respective change in capacitance between the proof mass and each respective electrode of the one or more electrodes; and
   determine, based on the information indicative of each respective change in capacitance between the proof mass and each respective electrode, characteristics of the electric field in at least two dimensions; and
   an electric dipole coupled to the proof mass,
   wherein the electric dipole includes a dielectric material, and wherein the control circuit is configured to selectively polarize the dielectric material along a first polarization axis and a second polarization axis, the first polarization axis being orthogonal to the second polarization axis.

2. The sensor system of claim 1, wherein the electric field (Original) detector is removably coupled to the first substrate.

3. The sensor system of claim 2, further comprising an adhesive coupled to the first substrate, the first substrate being configured to be removably coupled to the user.

4. A sensor system comprising:
   a first substrate configured to be coupled to a user;
   an electric field detector to detect an electric field generated by the user, the electric field detector being coupled to the first substrate and comprising:
   a second substrate;
   a proof mass positioned above the second substrate;
   one or more electrodes coupled to the second substrate; and
   a control circuit coupled to the one or more electrodes, the control circuit being configured to determine a respective change in capacitance between the proof mass and each respective electrode of the one or more electrodes responsive to torsional movement of the proof mass in response to the electric field; and
   a controller coupled to the first substrate and to the electric field detector, the controller being configured to:
   receive, from the electric field detector, information indicative of each respective change in capacitance between the proof mass and each respective electrode of the one or more electrodes; and
   determine, based on the information indicative of each respective change in capacitance between the proof mass and each respective electrode, characteristics of the electric field in at least two dimensions; and
   an electric dipole coupled to the proof mass, the electric dipole being polarized along a polarization axis,
   wherein the proof mass is configured to:
   rotate about a first torque axis orthogonal to the polarization axis responsive to the electric field having a first vector component aligned with a first electric field axis, the first electric field axis being orthogonal to the polarization axis and the first torque axis; and
   rotate about a second torque axis orthogonal to the polarization axis responsive to the electric field having a second vector component aligned with a second electric field axis, the second electric field axis being orthogonal to the polarization axis and the second torque axis,
   wherein the second torque axis is parallel to the first electric field axis and the first torque axis is parallel to the second electric field axis.

5. The sensor system of claim 4, wherein the one or more electrodes includes a first set of one or more electrodes and a second set of one or more electrodes, the control circuit being configured to:
   determine a first change in capacitance between the proof mass and the first set of one or more electrodes responsive to torsional movement of the proof mass about the first torque axis; and
   determine a second change in capacitance between the proof mass and the second set of one or more electrodes responsive to torsional movement of the proof mass about the second torque axis.

6. The sensor system of claim 5, wherein the controller is further configured to determine, based on the first change in capacitance and the second change in capacitance, characteristics of the electric field along the first electric field axis and the second electric field axis.

7. The sensor system of claim 1, the proof mass being configured to:
   rotate about a first torque axis orthogonal to the first polarization axis responsive to receiving the electric field along a first electric field axis, the first electric field axis being orthogonal to the first polarization axis and the first torque axis;
   rotate about a second torque axis orthogonal to the first polarization axis responsive to receiving the electric field along a second electric field axis, the second electric field axis being orthogonal to the first polarization axis and the second torque axis; and
   rotate about a third torque axis orthogonal to the second polarization axis responsive to receiving the electric field along a third electric field axis, the third electric field axis being orthogonal to the second polarization axis and the third torque axis,
   wherein the first torque axis is parallel to the second electric field axis and one of the third electric field axis and the second polarization axis, the second torque axis is parallel to the first electric field axis and one of the third electric field axis and the second polarization axis, and the third torque axis is parallel to the first polarization axis.

8. The sensor system of claim 7, wherein the one or more electrodes includes a first set of one or more electrodes, a second set of one or more electrodes, and a third set of one or more electrodes, the control circuit being configured to:
   determine a first change in capacitance between the proof mass and the first set of one or more electrodes responsive to torsional movement of the proof mass about the first torque axis;

determine a second change in capacitance between the proof mass and the second set of one or more electrodes responsive to torsional movement of the proof mass about the second torque axis; and determine a third change in capacitance between the proof mass and the third set of one or more electrodes responsive to torsional movement of the proof mass about the third torque axis.

9. The sensor system of claim 8, wherein the controller is further configured to determine, based on the first change in capacitance, the second change in capacitance, and the third change in capacitance, characteristics of the electric field along the first electric field axis, the second electric field axis, and the third electric field axis.

10. The sensor system of claim 1, further comprising a first set of polarization electrodes and a second set of polarization electrodes coupled to the dielectric material, the first set of polarization electrodes being positioned along the first polarization axis and the second set of polarization electrodes being positioned along the second polarization axis.

11. The sensor system of claim 10, wherein the control circuit is configured to:
generate a first voltage difference across the first set of polarization electrodes to polarize the dielectric material along the first polarization axis; and
generate a second voltage difference across the second set of polarization electrodes to polarize the dielectric material along the second polarization axis.

12. The sensor system of claim 11, wherein generating the first voltage difference includes applying a first voltage to the first set of polarization electrodes at a first frequency, and wherein generating the second voltage difference includes applying a second voltage to the second set of polarization electrodes at a second frequency, the first frequency being different than the second frequency.

13. The sensor system of claim 1, wherein the electric field detector is configured to detect an electric field generated by a muscle of the user.

14. The sensor system of claim 13, wherein the controller is configured to determine characteristics of an electric field generated by a heart of the user.

15. The sensor system of claim 1, wherein the controller is configured to determine characteristics of the electric field in three orthogonal dimensions.

16. The sensor system of claim 1, further comprising a movement sensor configured to determine information indicative of movement of the electric field detector, the controller being coupled to the movement sensor and being configured to:
receive the information indicative of the movement of the electric field detector; and determine the characteristics of the electric field based on the information indicative of each respective change in the capacitance between the proof mass and each respective electrode of the one or more electrodes and the information indicative of the movement of the electric field detector.

17. The sensor system of claim 16, wherein determining the characteristics of the electric field based on the information indicative of each respective change in the capacitance between the proof mass and each respective electrode of the one or more electrodes and the information indicative of the movement of the electric field detector includes identifying motion artifacts caused by the movement of the electric field detector.

18. An electric field detector to detect an electric field generated by a user, the electric field detector comprising:
a substrate;
a proof mass positioned above the substrate;
a plurality of electrodes coupled to the substrate, the plurality of electrodes including a first set of one or more electrodes and a second set of one or more electrodes; and
a control circuit coupled to the plurality of electrodes, the control circuit being configured to determine a first change in capacitance between the proof mass and the first set of one or more electrodes responsive to torsional movement of the proof mass about a first torque axis and to determine a second change in capacitance between the proof mass and the second set of one or more electrodes responsive to torsional movement of the proof mass about a second torque axis orthogonal to the first torque axis in response to being exposed to the electric field generated by the user; and
an electric dipole coupled to the proof mass,
wherein the electric dipole includes a dielectric material, and wherein the control circuit is configured to selectively polarize the dielectric material along a first polarization axis and a second polarization axis, the first polarization axis being orthogonal to the second polarization axis.

* * * * *